(12) United States Patent
Fischell et al.

(10) Patent No.: US 10,736,524 B2
(45) Date of Patent: *Aug. 11, 2020

(54) INTRAVASCULAR CATHETER WITH PERI-VASCULAR NERVE ACTIVITY SENSORS

(71) Applicant: Ablative Solutions, Inc., San Jose, CA (US)

(72) Inventors: David R. Fischell, Fair Haven, NJ (US); Tim A. Fischell, Kalamazoo, MI (US); Vartan Ghazarossian, Menlo Park, CA (US); Steven Almany, Bloomfield Hills, MI (US)

(73) Assignee: Ablative Solutions, Inc., San Jose, CA (US)

( * ) Notice: Subject to any disclaimer, the term of this patent is extended or adjusted under 35 U.S.C. 154(b) by 313 days.

This patent is subject to a terminal disclaimer.

(21) Appl. No.: 15/940,178

(22) Filed: Mar. 29, 2018

(65) Prior Publication Data

US 2018/0279894 A1 Oct. 4, 2018

Related U.S. Application Data

(63) Continuation of application No. 14/063,907, filed on Oct. 25, 2013, now Pat. No. 9,931,046.

(51) Int. Cl.
*A61B 5/04* (2006.01)
*A61M 3/02* (2006.01)
(Continued)

(52) U.S. Cl.
CPC ........ *A61B 5/04001* (2013.01); *A61B 5/4035* (2013.01); *A61B 5/6848* (2013.01);
(Continued)

(58) Field of Classification Search
CPC . A61B 5/0422; A61B 18/1492; A61B 5/6852; A61B 18/00267; A61B 5/6859;
(Continued)

(56) References Cited

U.S. PATENT DOCUMENTS

| 4,578,061 A | 3/1986 | Lemelson |
| 4,798,595 A | 1/1989 | Anderson et al. |

(Continued)

FOREIGN PATENT DOCUMENTS

| CN | 1147964 | 4/1997 |
| CN | 1494399 | 5/2004 |

(Continued)

OTHER PUBLICATIONS

U.S. Appl. No. 15/711,162, filed Sep. 21, 2017, Fischell, et al.
(Continued)

*Primary Examiner* — Eun Hwa Kim
*Assistant Examiner* — Brian M Antiskay
(74) *Attorney, Agent, or Firm* — Knobbe, Martens, Olson & Bear, LLP

(57) ABSTRACT

An intravascular catheter for peri-vascular nerve activity sensing or measurement includes multiple needles advanced through supported guide tubes (needle guiding elements) which expand with open ends around a central axis to contact the interior surface of the wall of the renal artery or other vessel of a human body allowing the needles to be advanced though the vessel wall into the perivascular space. The system also may include means to limit and/or adjust the depth of penetration of the needles. The catheter also includes structures which provide radial and lateral support to the guide tubes so that the guide tubes open uniformly and maintain their position against the interior surface of the vessel wall as the sharpened needles are advanced to penetrate into the vessel wall. The addition of an injection lumen
(Continued)

at the proximal end of the catheter and openings in the needles adds the functionality of ablative fluid injection into the perivascular space for an integrated nerve sending and ablation capability.

18 Claims, 14 Drawing Sheets

(51) Int. Cl.

| | | |
|---|---|---|
| *A61M 31/00* | (2006.01) | |
| *A61B 5/00* | (2006.01) | |
| A61B 18/14 | (2006.01) | |
| A61B 18/00 | (2006.01) | |
| A61B 17/32 | (2006.01) | |
| A61B 18/18 | (2006.01) | |
| A61B 18/02 | (2006.01) | |
| A61B 18/04 | (2006.01) | |
| A61M 25/00 | (2006.01) | |
| A61B 5/20 | (2006.01) | |
| A61B 90/00 | (2016.01) | |

(52) U.S. Cl.
CPC ............ *A61B 5/6852* (2013.01); *A61B 5/201* (2013.01); *A61B 18/1477* (2013.01); *A61B 18/1492* (2013.01); *A61B 18/1815* (2013.01); *A61B 2017/320069* (2017.08); *A61B 2018/00214* (2013.01); *A61B 2018/00434* (2013.01); *A61B 2018/00577* (2013.01); *A61B 2018/00642* (2013.01); *A61B 2018/00839* (2013.01); *A61B 2018/0212* (2013.01); *A61B 2018/046* (2013.01); *A61B 2018/1425* (2013.01); *A61B 2090/3966* (2016.02); *A61M 2025/0095* (2013.01)

(58) Field of Classification Search
CPC ................ A61B 19/5244; A61B 5/065; A61B 2018/00214; A61B 2017/003; A61B 5/6848; A61B 2018/1425
USPC ................ 600/372–375, 378, 381, 466–467; 607/115, 118–119, 126, 128, 133; 604/32–42
See application file for complete search history.

(56) References Cited

U.S. PATENT DOCUMENTS

| | | |
|---|---|---|
| 5,304,141 A | 4/1994 | Johnson et al. |
| 5,354,279 A | 10/1994 | Hofling |
| 5,385,562 A | 1/1995 | Adams et al. |
| 5,419,777 A | 5/1995 | Hofling |
| 5,464,395 A | 11/1995 | Faxon et al. |
| 5,474,102 A | 12/1995 | Lopez |
| 5,551,426 A | 9/1996 | Hummel et al. |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,800,379 A | 9/1998 | Edwards |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Desai |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |
| 8,983,595 B2 | 3/2015 | Levin et al. |
| 9,011,879 B2 | 4/2015 | Seward |
| 9,056,185 B2 | 6/2015 | Fischell et al. |
| 9,125,661 B2 | 9/2015 | Deem et al. |
| 9,131,978 B2 | 9/2015 | Zarins et al. |

(56) References Cited

U.S. PATENT DOCUMENTS

| | | |
|---|---|---|
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |
| 9,814,873 B2 | 11/2017 | Zarins et al. |
| 9,895,195 B2 | 2/2018 | Zarins et al. |
| 9,907,611 B2 | 3/2018 | Levin et al. |
| 2001/0037065 A1 | 11/2001 | Graf et al. |
| 2002/0010439 A1 | 1/2002 | Miller |
| 2002/0052577 A1 | 5/2002 | Shimazaki et al. |
| 2002/0082584 A1 | 6/2002 | Rosenman et al. |
| 2002/0120238 A1 | 8/2002 | McGuckin et al. |
| 2002/0177846 A1 | 11/2002 | Mulier et al. |
| 2002/0183738 A1 | 12/2002 | Chee et al. |
| 2003/0032929 A1 | 2/2003 | McGuckin, Jr. |
| 2003/0171723 A1 | 9/2003 | Ponzi |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0224118 A1 | 10/2006 | Morris et al. |
| 2006/0271111 A1 | 11/2006 | Demarais et al. |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0045890 A1 | 2/2008 | Seward et al. |
| 2008/0051756 A1 | 2/2008 | Makower et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0305546 A1 | 12/2010 | Seward et al. |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2012/0053604 A1 | 3/2012 | DiCaprio |
| 2012/0071832 A1 | 3/2012 | Bunch |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |
| 2015/0132409 A1 | 5/2015 | Stein et al. |
| 2015/0202220 A1 | 7/2015 | Stein et al. |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0354137 A1 | 12/2016 | Fischell et al. |
| 2017/0304594 A1 | 10/2017 | Fischell et al. |
| 2017/0326363 A1 | 11/2017 | Deem et al. |
| 2017/0332926 A1 | 11/2017 | Fischell et al. |

FOREIGN PATENT DOCUMENTS

| | | |
|---|---|---|
| CN | 1927130 | 3/2007 |
| EP | 0834288 | 4/1998 |

(56) References Cited

FOREIGN PATENT DOCUMENTS

| | | |
|---|---|---|
| EP | 0876805 | 8/2006 |
| JP | H07-509389 | 10/1995 |
| JP | H08-89582 | 4/1996 |
| JP | 2001-527428 | 12/2001 |
| JP | 2002-510229 | 4/2002 |
| JP | 2002-542901 | 12/2002 |
| JP | 2004-516042 | 6/2004 |
| JP | 2005-40599 | 2/2005 |
| JP | 2008-506500 | 3/2008 |
| JP | 09-509865 | 3/2009 |
| WO | WO 94/04220 | 3/1994 |
| WO | WO 95/13752 | 5/1995 |
| WO | WO 2004/030740 | 4/2004 |
| WO | WO 2007/121143 | 10/2007 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |

OTHER PUBLICATIONS

U.S. Appl. No. 15/917,532, filed Mar. 9, 2018, Fischell, et al.
U.S. Appl. No. 15/947,618, filed Apr. 6, 2018, Fischell, et al.
U.S. Appl. No. 15/947,619, filed Apr. 6, 2018, Fischell, et al.
U.S. Appl. No. 15/947,626, filed Apr. 6, 2018, Fischell, et al.
U.S. Appl. No. 15/947,460, filed Apr. 6, 2018, Fischell, et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses to Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.
F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.
Gado et al., "Intra-articular guanethidine injection for resistant shoulder pain: a preliminary double blind study of a novel approach" Annals of the Rheumatic Disease, 1996, p. 199-201.

Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction in Single Sympathetic Nerve Firing After Renal Denervation in Patients With Resistant Hypertension", Nov. 19, 2012, p. 856-864.
Hering et al., "Substantial Reduction in Single Sympathetic Nerve Firing After Renal Denervation in Patients With Resistant Hypertension", Nov. 19, 2012 in 15 pages.
Hsu et al., "The Use of Intravenous Guanethidine Block in the Management of Reflex Sympathic Dystrophy Syndrome of the Hand." Second Congress of the Hong Kong Orthopaedic Association, Nov. 1982, p. 93-105.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.
"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
National Institute for Health and Care Excellence. Hypertension in adults: diagnosis and management. Aug. 24, 2011, NICE, CG127.
Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.
Roytta et al., Taxol-induced neuropathy: short-term effects of local injection (Journal of Neurocytology 13, 1984), p. 685-701.
S J .Doletskiy et al. "Vysokochastotnaj Elektrotekhnika", M., 7-10 "Meditsina", 1980, p. 48-50, fig. 18-19.
Trostel et al., Do renal nerves chronically influence renal function and arterial pressure in spinal rats? (The American Physiological Society 1992), p. 1265-1270.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
YA Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.
Zafonte et al., "Phenol and Alcohol Blocks for the Treatment of Spasticity", Physical medicine and rehabilitation clinics of North America, Nov. 2001, p. 817-832.
International Search Report and Written Opinion in PCT/US14/062043 dated Mar. 27, 2015 in 16 pages.
Extended Search Report in EP 14855452.0 dated May 22, 2017 in 7 pages.
International Search Report and Written Opinion in PCT/US16/65017 dated Aug. 14, 2017 in 9 pages.
Office Action for Chinese Patent Application 201480068510.0 dated Dec. 25, 2017 in 20 pages.

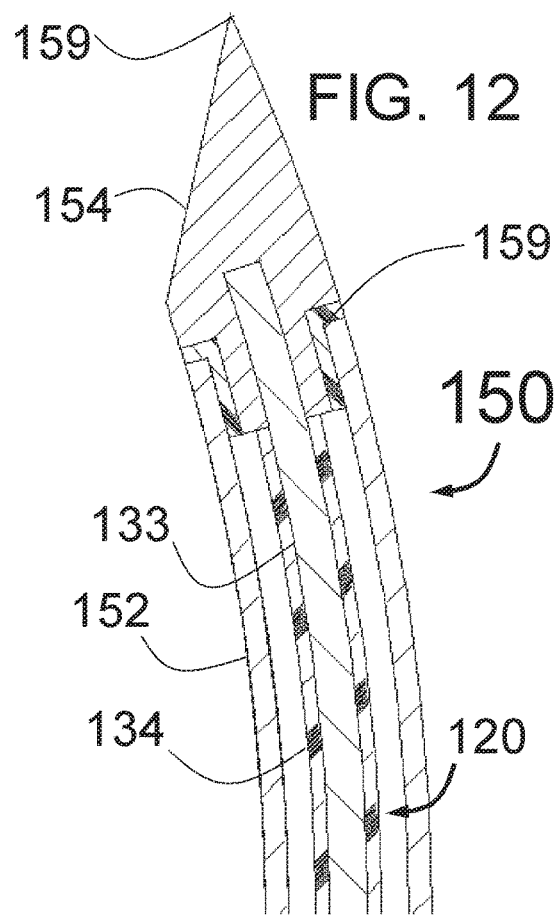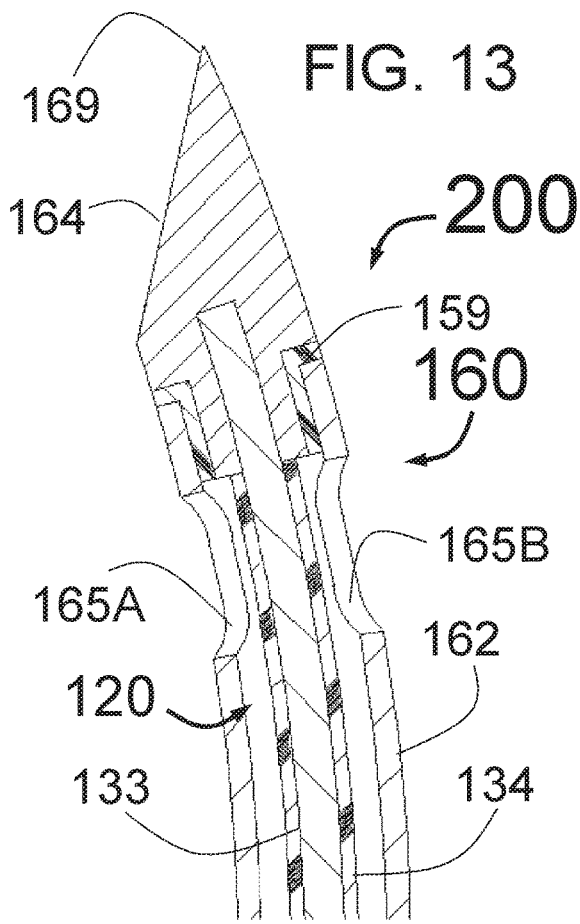

INTRAVASCULAR CATHETER WITH PERI-VASCULAR NERVE ACTIVITY SENSORS

INCORPORATION BY REFERENCE TO ANY PRIORITY APPLICATIONS

This application is a continuation of U.S. patent application Ser. No. 14/063,907, filed Oct. 25, 2013, and hereby incorporated by reference in its entirety. Any and all applications for which a foreign or domestic priority claim is identified in the Application Data Sheet as filed with the present application are hereby incorporated by reference under 37 CFR 1.57.

FIELD OF THE INVENTION

This invention is in the field of devices to ablate tissue and nerve fibers for the treatment of hypertension, congestive heart failure, and other disorders.

BACKGROUND OF THE INVENTION

It has been recognized that activity of the sympathetic nerves to the kidneys contributes to essential hypertension, which is the most common form of hypertension. Sympathetic stimulation of the kidneys may contribute to hypertension by several mechanisms, including the stimulation of the release of renin (which results in production of angiotensin II, a potent vasoconstrictor), increased renal reabsorption of sodium, at least in part related to increased release of aldosterone (which increases blood volume and therefore blood pressure), and reduction of renal blood flow, which also results in angiotensin II production.

Since the 1930s it has been known that injury or ablation of the sympathetic nerves in or near the outer layers of the renal arteries can dramatically reduce high blood pressure. As far back as 1952, alcohol has been used for tissue ablation in animal experiments. Specifically Robert M. Berne in "Hemodynamics and Sodium Excretion of Denervated Kidney in Anesthetized and Unanesthetized Dog" Am J Physiol, October 1952 171:(1) 148-158, describes applying alcohol on the outside of a dog's renal artery to produce denervation.

Ablation of renal sympathetic nerves to treat drug-resistant hypertension is now a proven strategy [Symplicity-HTN-2 Investigators, Lancet 2010]. In order for the procedure to be successful, renal nerves need to be ablated such that their activity is significantly diminished. One drawback of ablation procedures is the inability for the physician performing the procedure to ascertain during the procedure itself that the ablation has been successfully accomplished. The reason for this is that the nerves cannot be visualized during the procedure; therefore, the procedure must be performed in a "blind" fashion. The ablation procedure is invasive, requiring catheterization of the femoral artery, advancement of a catheter into the renal artery, administration of iodinated contrast agents, and radiation exposure. Furthermore, procedural success with currently available devices is far from universal. In a randomized, controlled clinical trial using radiofrequency ablation, 16% of patients failed to achieve even a 10 mmHg reduction in systolic blood pressure and 61% did not achieve a goal systolic blood pressure of <140 mmHg [Symplicity-HTN-2 Investigators, Lancet 2010].

The procedure must be performed in a catheterization laboratory or operative-type suite. The benefit-risk of this invasive procedure as well as its cost-benefit would be enhanced if procedural success could be assessed during the procedure. Assessing the technical success of the procedure during the procedure would allow the physician to perform additional ablation attempts and/or to adjust the technique as needed, which, in turn is expected to improve efficacy and to reduce the need to bring the patient back for a second procedure at additional cost and risks to the patient. The desired effect of renal sympathetic nerve ablation procedure is a lowering of blood pressure, with consequent reduction in the need for chronic antihypertensive drug treatment. Since the blood pressure lowering effect of the treatment does not occur immediately, the blood pressure measured in the catheterization laboratory also cannot act as a guide to the technical success of the procedure.

There are currently two basic methods to ablate renal sympathetic nerves: energy-based neural damage resulting from radiofrequency or ultrasonic energy delivery and chemical neurolysis. Both methods require percutaneous insertion of a catheter into the renal arteries. Radiofrequency-based methods transmit radiofrequency energy through the renal artery wall to ablate the renal nerves surrounding the blood vessel. Chemical neurolysis uses small gauge needles that pass through the renal artery wall to inject a neurolytic agent directly into the adventitial and/or periadvential area surrounding the blood vessel, which is where the renal sympathetic nerves entering and leaving the kidney (i.e., afferent and efferent nerves) are located.

Recent technology for renal denervation include energy delivery devices using radiofrequency or ultrasound energy, such as Simplicity™ (Medtronic), EnligHTN™ (St. Jude Medical) and One Shot system from Covidien, all of which are RF ablation catheters. There are potential risks using the current technologies for RF ablation to create sympathetic nerve denervation from inside the renal artery. The short-term complications and the long-term sequelae of applying RF energy from the inner lining (intima) of the renal artery to the outer wall of the artery are not well defined. This type of energy applied within the renal artery, and with transmural renal artery injury, may lead to late stenosis, thrombosis, renal artery spasm, embolization of debris into the renal parenchyma, or other problems related to the thermal injury to the renal artery. There may also be uneven or incomplete sympathetic nerve ablation, particularly if there are anatomic anomalies, or atherosclerotic or fibrotic disease in the intima of the renal artery, the result being that there is non-homogeneous delivery of RF energy. This could lead to treatment failures, or the need for additional and dangerous levels of RF energy to ablate the nerves that run along the adventitial plane of the renal artery. Similar safety and efficacy issues may also be a concern with the use of ultrasound. The Simplicity™ system for RF delivery also does not allow for efficient circumferential ablation of the renal sympathetic nerve fibers. If circumferential RF energy were applied in a ring segment from within the renal artery (energy applied at intimal surface to damage nerves in the outer adventitial layer) this could lead to even higher risks of renal artery stenosis from the circumferential and transmural thermal injury to the intima, media and adventitia. Finally, the "burning" of the interior wall of the renal artery using RF ablation can be extremely painful. The long duration of the RF ablation renal denervation procedure requires sedation and, at times, extremely high doses of morphine or other opiates, and anesthesia, close to general anesthesia, to control the severe pain associated with repeated burning of the vessel wall. This is especially difficult to affect with any energy based system operating from inside the renal artery as the C-fibers which are the pain nerves are located within or close to the media layer of the artery. Thus, there are numerous and substantial limitations of the current approach using RF-based renal sympathetic denervation. Similar limitations apply to ultrasound or other energy delivery techniques.

The Bullfrog® micro infusion catheter described by Seward et al in U.S. Pat. Nos. 6,547,803 and 7,666,163, which uses an inflatable elastic balloon to expand a single needle against the wall of a blood vessel, could be used for the injection of a chemical ablative solution such as guanethidine or alcohol but it would require multiple applications as those patents do not describe or anticipate the circumferential delivery of an ablative substance around the entire circumference of the vessel. The greatest number of needles shown by Seward is two, and the two needle version of the Bullfrog® would be hard to miniaturize to fit through a small guiding catheter to be used in a renal artery particularly if needles of adequate length to penetrate to the periadventitia were used. If only one needle is used, controlled and accurate rotation of any device at the end of a catheter is difficult at best and could be risky if the subsequent injections are not evenly spaced. This device also does not allow for a precise, controlled and adjustable depth of delivery of a neuroablative agent. This device also may have physical constraints regarding the length of the needle that can be used, thus limiting the ability to inject agents to an adequate depth, particularly in diseased renal arteries with thickened intima. All of these limitations could lead to incomplete denervation and treatment failure. Another limitation of the Bullfrog® is that inflation of a balloon within the renal artery can induce transient renal ischemia and possibly late vessel stenosis due to balloon injury of the intima and media of the artery, as well as causing endothelial cell denudation.

Jacobson and Davis in U.S. Pat. No. 6,302,870 describe a catheter for medication injection into the interior wall of a blood vessel. While Jacobson includes the concept of multiple needles expanding outward, each with a hilt to limit penetration of the needle into the wall of the vessel, his design depends on rotation of the tube having the needle at its distal end to allow it to get into an outwardly curving shape. The hilt design shown of a small disk attached a short distance proximal to the needle distal end has a fixed diameter which will increase the total diameter of the device by at least twice the diameter of the hilt so that if the hilt is large enough in diameter to stop penetration of the needle, it will significantly add to the diameter of the device. Using a hilt that has a greater diameter than the tube, increases the device profile, and also prevents the needle from being completely retracted back inside the tubular shaft from which it emerges, keeping the needles exposed and potentially allowing accidental needlestick injuries to occur. For either the renal denervation or atrial fibrillation application, the length of the needed catheter would make control of such rotation difficult. In addition, the hilts, which limit penetration, are a fixed distance from the distal end of the needles. There is no built in adjustment on penetration depth which may be important if one wishes to selectively target a specific layer in a vessel or if one needs to penetrate all the way through to the volume of tissue outside of the adventitia in vessels with different wall thicknesses. Jacobson also does not envision use of the injection catheter for denervation. Finally, FIG. 3 of the Jacobson patent shows a sheath over expandable needles without a guide wire, and the sheath has an open distal end which makes advancement through the vascular system more difficult. Also, because of the hilts, if the needles were withdrawn completely inside of the sheath they could get stuck inside the sheath and be difficult to push out. The complexity of this system might also lead to inadequate, or incomplete renal denervation.

McGuckin in U.S. Pat. No. 7,087,040 describes a tumor tissue ablation catheter having three expandable tines for injection of fluid that exit a single needle. The tines expand outwardly to penetrate the tissue. The McGuckin device has an open distal end that does not provide protection from inadvertent needle sticks from the sharpened tines. In addition, the McGuckin device depends on the shaped tines to be of sufficient strength so that they can expand outwardly and penetrate the tissue. To achieve such strength, the tines would have to be so large in diameter that severe extravascular bleeding would often occur when the tines would be retracted back following fluid injection for a renal denervation application. There also is no workable penetration limiting mechanism that will reliably set the depth of penetration of the distal opening from the tines with respect to the interior wall of the vessel, nor is there a preset adjustment for such depth. For the application of treating liver tumors, the continually adjustable depth of tine penetration may make sense since multiple injections at several depths might be needed. However, for renal denervation, the ability to accurately adjust the depth or have choice of penetration depth when choosing the device to be used is important so as to not infuse the ablative fluid too shallow and injure the media of the renal artery or too deep and thus miss the nerves that are in the adventitial and peri-adventitial layers of the renal artery.

Fischell et al in U.S. patent application Ser. Nos. 13/216,495, 13/294,439 and 13/342,521 describe several methods of using expandable needles to deliver ablative fluid into or deep to the wall of a target vessel. Each of these applications is hereby incorporated by reference in its entirety. There are two types of embodiments of Ser. Nos. 13/216,495, 13/294,439 and 13/342,521 applications, those where the needles alone expand outwardly without support from any other structure and those with guide tubes that act as guiding elements to support the needles as they are advanced into the wall of a target vessel. The limitation of the needle alone designs are that if small enough diameter needles are used to avoid blood loss following penetration through the vessel wall, then the needles may be too flimsy to reliably and uniformly expand to their desired position. The use of a cord or wire to connect the needles together in one embodiment helps some in the area. The use of guide tubes as described in the Fischell application Ser. Nos. 13/294,439 and 13/342,521 greatly improves this support, but the unsupported guide tubes themselves depend on their own shape to ensure that they expand uniformly and properly center the distal portion of the catheter. Without predictable catheter centering and guide tube expansion it may be challenging to achieve accurate and reproducible needle penetration to a targeted depth. More recently in U.S. patent application Ser. No. 13/752,062, Fischell et al describe self-expanding and manually expandable ablation devices that have additional structures to support the needle guiding elements/guide tubes. The Ser. No. 13/752,062 designs for a Perivascular Tissue Ablation Catheter (PTAC) will be referenced throughout this disclosure.

While the prior art has the potential to produce ablation of the sympathetic nerves surrounding the renal arteries and thus reduce the patient's blood pressure, none of the prior art includes sensors or additional systems to monitor the activity of the sympathetic nerves being ablated. Such measurement would be advantageous as it could provide immediate feedback relative to the effectiveness of the ablation procedure and indicate if an additional ablation administration may be needed. For example, additional energy delivery or additional ablative fluid delivery could be administered if the nerves are still conducting (electrical) activity.

It is technically feasible to measure renal sympathetic activity directly or indirectly in vivo using several methods. Such measurements have been accomplished in unrestrained conscious mice [Hamza and Hall, Hypertension 2012], dogs [Chimushi, et al. Hypertension 2013], and rabbits [Doward, et al. *J Autonomic Nervous System* 1987].

In the study by Hamza and Hal, an electrode was surgically placed directly on the renal nerves and left in place while recordings were made over up to 5 days. The recordings of renal sympathetic nerve activity were confirmed by observations of appropriate responses to conditions of rest and activity, pharmacologic manipulation of blood pressure with sodium nitroprusside and phenylephrine, and by neural ganglionic blockade. Doward, et al also used surgical placement of an electrode to directly measure renal sympathetic nerve activity. The recordings of renal sympathetic nerve activity were confirmed by observations of appropriate responses to baroreceptor stimulation, angiotensin, central and peripheral chemoreceptors. In the study by Chimushi, renal sympathetic nerves were stimulated from within the renal artery and evidence of activity was indirectly evaluated based on blood pressure response to neural stimulation.

SUMMARY OF THE INVENTION

The present application discloses a Sympathetic Nerve Sensing Catheter (SNSC) that senses perivascular renal sympathetic nerve activity and can be complementary to a non-sensing renal denervation device whether it is a chemical device such as the PTAC of Fischell or an energy delivery device such as SIMPLICITY, or even when using external sources of ablation such as surgical intervention, externally delivered ultrasound (Kona), etc.

Also disclosed is Peri-vascular Nerve Ablation and Sensing Catheter (PNASC), that is capable of delivering an ablative fluid to produce circumferential damage in the tissue that is in the outer layer or beyond the outer layer of a vessel of a human body. The PNASC also includes sensors for sensing the activity of the sympathetic nerves that lie outside of the external elastic lamina of the renal artery. The integrated PNASC has the advantage of saving time at the cost of adding complexity to the pure ablation device. The SNSC requires a separate renal denervation device but has a larger potential market for use with other, potentially less effective and less predictable renal denervation devices, such as those that ablate nerves using RF.

The nerve ablation procedure using peri-vascular injection by the prior art catheters disclosed by Fischell or the PNASC disclosed herein, can be accomplished in a relatively short time as compared with RF ablation catheters, and also has the advantage of using only a single disposable catheter, with no additional, external, capital equipment. It will also allow the use of short acting sedating agents like Versed, permit delivery of local anesthetic into the adventitial space before ablation and may eliminate the need for large doses of narcotics to reduce or eliminate patient discomfort and pain, that are typically required during energy based ablation procedures.

While the primary focus of use of PNASC is in the treatment of hypertension and congestive heart failure by renal denervation, the PNASC which has the ability to sense sympathetic nerve activity, and could be used in conjunction with energy-based renal denervation devices to enhance the effectiveness of the renal denervation.

Much of the structure of the SNSC and PNASC can in one implementation be similar to the manually expandable Perivascular Tissue Ablation Catheter (PTAC) designs of Fischell et al in U.S. patent application Ser. No. 13/752,062 shown in FIGS. 2 through 11. Specifically, the SNSC and PNASC can use the same proximal control for guide tubes and needles as the Fischell device as well as the same guide tubes and radial and lateral support structures. Several versions of the SNSC will be included. In one version the injector tubes with distal injection needles of Fischell device are replaced by a solid sharpened wire that is insulated except for its tip. In a second embodiment, the PTAC structure shown in FIGS. 2-10 would have the radiopaque wire inside the injector needles removed and an electrode with a proximal insulated wire would be attached within the distal end of the injection needle. Ideally, the electrode would be of gold or platinum or another radiopaque metal to improve radiopacity. Two configurations of this will be disclosed: one where the electrode lies completely within the lumen of the injection needle and a second embodiment where the electrode extends distally beyond the lumen of the injector tube and forms at least part of the sharpened needle. Each of the proximal insulated wires then run through the injector tube lumen into the lumen of the inner tube and finally exit out of the lumen at the proximal end of the SNSC. There, the wires can be attached to an electronics module for measuring nerve activity and identifying changes that indicate when successful or unsuccessful nerve ablation has occurred.

Embodiments of the PNASC would have injection ports such as side holes in the injector tube just proximal to the electrode or longitudinal holes through the electrode. These holes allow ablative fluid injected from the proximal injection port to effuse from the distal end of each needle into the perivascular space. At the proximal end, the wires could exit though the side of the injection port or exit distally through the injection port lumen where a Tuohy-Borst fitting would seal around the wires with the side port in the Tuohy-Borst used for infusion of the ablative fluid.

Specifically, the PNASC like the prior Fischell PTAC is a percutaneously introduced catheter with two or more injection needles for the delivery of ablative fluid. The needles expand outwardly from the catheter and penetrate through the wall of the renal artery into the peri-vascular space where the sympathetic nerves are located.

Sensing of the nerve activity may be done between pairs of sensors located near or at the distal ends of the needles (PNASC) or wires (SNSC) or between a sensor located near or at the distal end of a needle/wire and a common ground. Such a common ground could be all or a portion of the outer tube of the PNASC/SNSC, a ring located on the outside of the PNASC/SNSC, a portion of the distal nose of the PNASC/SNSC or an integrated or separate guide wire. The common ground might also be an EKG electrode placed on the body over the location of the renal artery. The PTAC designs of Fischell et al have numerous structures that would function as such a common ground including the fixed guide wire, the tapered distal section, the outer tubes, the intraluminal centering mechanism, the guide tubes or guide tube marker bands or the outer tube extension.

The preferred embodiment would either not have a common ground or would use the EKG electrode as this will allow a smaller diameter configuration.

Another embodiment of the PNASC has the sensors separate but inside the distal lumen of the injection needles. For example, if the radiopaque wires that lie inside of the injection needles in the Fischell PTAC designs, were insulted and their wire tips which are located inside of the distal end of the needles are bare to act as electrodes, then the wires themselves would be the sensors. As with the concept using the needles as electrodes, each wire would need a metallic contact (or wire) that runs to the proximal end of the catheter where they would need to be accessible and connectable to external equipment. It would also be preferred to coat the inside of the distal tip of the injection needles to prevent the wire tip from shorting to the inside of the metallic needle.

It is also envisioned that with a separate control mechanism, these wires could be advanced distally from the distal end of the injection needles, further into the perivascular space.

A third embodiment could have one or more additional expandable structures that could deliver a sharpened insulated wire through the arterial wall into the periadventitial space with control of the expansion either by the same or separate mechanisms that expand and support the injection needles. For example, four guide tubes similar to those in the PTAC shown by Fischell et al in U.S. patent application Ser. No. 13/752,062, could expand outwardly from the shaft of the PNASC catheter. Four sharpened structures would then be advanced through the guide tubes through the renal artery wall and into the periadventitial space. Two of the structures could be injection needles for delivery of ablative fluid and two could be sharpened wires for sensing the effectiveness of the ablation. Preferably, the sensors are circumferentially offset from the injection needles. In one two needle implementation, the offset is about 90°, and in a 3 needle implementation, the offset is about 60°. This configuration could be ideal as the sensors in a two needle embodiment are at 90 degrees to the injection needles where the effect of the injection would be least. In other words, if the nerves are appropriately damaged as sensed by the points furthest from the point of ablation then the nerves everywhere else around the ring of ablation should be adequately ablated. Configurations with more or less than 4 penetrating structures can also be envisioned.

This type of PNASC integrated ablation and sensing system may also have major advantages over other current technologies by allowing highly efficient, and reproducible peri-vascular circumferential ablation of the muscle fibers and conductive tissue in the wall of the pulmonary veins near or at their ostium into the left atrium of the heart, or in the pulmonary arteries in the case of nerve ablation to treat pulmonary arterial hypertension. Such ablation could interrupt atrial fibrillation (AF) and other cardiac arrhythmias. For the AF application, nerve and/or cardiac myocyte electrical activity measurement could be an effective technique to provide immediate assessment of the success of an AF ablation procedure. Other potential applications of this approach, such as pulmonary artery nerve ablation, or others, may also become evident from the various teachings of this patent.

Like the earlier Fischell inventions for the treatment of hypertension, the SNSC/PNASC of the present application discloses a small diameter catheter, which includes multiple expandable injector tubes having sharpened injection needles at or near their distal ends that are advanced through guide tubes designed to support and guide the needles into and through the inner layers of the target vessel. While this application concentrates on manually expandable versions of the SNSC and PNASC, it is envisioned that similar electrodes could be used with the self-expandable versions of the Fischell prior designs.

The present invention PNASC can also include any one, combinations, or all of the primary features of the self-expandable and balloon expandable embodiments of the Fischell et al PTAC application Ser. No. 13/752,062 including but not limited to:

Needle guiding elements/guide tubes to support the expandable injection needles.
Mechanical support structures to support the needle guiding elements,
Limited catheter internal volume or dead space,
Radiopaque markers on the catheter, guide tubes and needles,
Penetration limiting mechanisms,
Depth of penetration adjustment mechanisms,
Proximal handle for control of catheter activation including an injection port,
Matched radii of curvature between the injector tubes and guide tubes,
Methods including injection of an anesthetic agent before the ablation.

This disclosure also anticipates the use of very small gauge needles (smaller than 25 gauge) to penetrate the arterial wall, such that the needle penetration could be safe, even if targeted to a volume of tissue that is beyond the adventitial layer of the aorta, a pulmonary artery or vein, or renal artery, or prostatic urethra. It is also anticipated that the distal needle could be a cutting needle or a coring needle. With a cutting needle the injection egress/distal opening ports could be small injection holes (pores) cut into the sides of the injector tubes or distal needle, proximal to the cutting needle tip. A Huber type needle could also be used. There are preferably at least 2 injector tubes but 3 to 8 tubes may be more appropriate, depending on the diameter of the vessel to be treated and the ability of the injected ablative fluid to spread within the peri-vascular space. For example, in a 5-7 mm diameter renal artery, 3 needles should be functional if ethanol is the ablative fluid.

The preferred embodiment of the present disclosure PNASC would use ethanol as the ablative fluid because this fluid is agrophobic, hygroscopic, lipophilic, and spreads quickly in the peri-vascular space. Therefore, only 3 needles are needed to create circumferential delivery of this ablative agent, which allows one to use a smaller diameter device. It is also envisioned that use of ethanol or another alcohol plus another neurotoxic agent could also enhance the spread of the ablative agent in the peri-vascular space.

While this disclosure will show both SNSC and PNASC to include a fixed distal guide wire, it is envisioned that a separate guide wire could be used with the catheter designed to be either an over-the-wire configuration where the guide wire lumen runs the entire length of the catheter or a rapid exchange configuration where the guide wire exits the catheter body at a proximal guide wire port positioned at least 10 cm proximal to the distal end of the catheter and runs outside of the catheter shaft for its proximal section. It is also envisioned that one could use a soft and tapered distal tip, even without a distal guidewire, for some applications.

The fixed wire version, or the version with the soft tapered distal tip without a guidewire are the preferred embodiments, as they would have the smallest distal diameter. Just proximal to the fixed wire is a tapered distal portion of the SNAC/PNASC.

It is also envisioned that one could attach at the proximal end of the SNAC/PNASC, the wires leading to two or more of the expandable electrodes to an electrical or RF source to deliver electric current or RF energy to perform tissue and/or nerve ablation. This could provide the ideal configuration for RF energy based renal denervation as the electrodes deliver the energy outside of the medial layer of the renal artery, and the normal intimal and medial wall structures would be cooled by blood flow. This configuration should dramatically reduce the damage to the artery as compared with intraluminal RF ablation. Even more important is that the sympathetic nerves to be ablated are quite deep beyond the outside of the media of the artery while the pain nerves are within or close to the media. Therefore an energy based denervation from electrodes deep to the outside of the media will be dramatically less painful than energy based ablation from inside of the renal artery.

Thus, the same electrodes can be used in a first mode to ablate nerves or other tissue, and also in a second mode to evaluate the electrical characteristics at the treatment site.

It is also envisioned that the PNASC device could utilize one, or more than one neuroablative substances to be injected simultaneously, or in a sequence of injections, in order to optimize permanent sympathetic nerve disruption in a segment of the renal artery (neurotmesis). The anticipated neurotoxic agents that could be utilized include but are not limited to ethanol, phenol, glycerol, local anesthetics in relatively high concentration (e.g., lidocaine, or other agents such as bupivicaine, tetracaine, benzocaine, etc.), anti-arrhythmic drugs that have neurotoxicity, botulinum toxin, digoxin or other cardiac glycosides, guanethidine, heated fluids including heated saline, hypertonic saline, hypotonic fluids, KCl or heated neuroablative substances such as those listed above.

It is also envisioned that the ablative substance can be hypertonic fluids such as hypertonic saline (extra salt) or hypotonic fluids such as distilled water. These could cause damage to the nerves and could be as effective as alcohol or specific neurotoxins. These can also be injected hot, or cold or at room temperature. The use of distilled water, hypotonic saline or hypertonic saline with an injection volume of less than 1 ml eliminates one step in the use of the PNASC because small volumes of these fluids should not be harmful to the kidney and so the need to completely flush the ablative fluid from the PNASC with normal saline to prevent any of the ablative fluid getting into the renal artery during catheter withdrawal is no longer needed. This means there would be only one fluid injection step per artery instead of two if a more toxic ablative fluid were used.

It is also envisioned that the PNASC catheter could be connected to a heated fluid or steam source to deliver high temperature fluids to ablate or injure the target tissue or nerves. The heated fluid could be normal saline, hypertonic fluid, hypotonic fluid alcohol, phenol, lidocaine, or some other combination of fluids. Injection of hot or vaporized normal saline, hypertonic saline, hypotonic saline, ethanol, distilled water or other fluids via the needles could also be performed in order to achieve thermal ablation of target tissue or nerves at and around the needle injection sites.

The present disclosure also envisions use of anesthetic agents such as lidocaine which if injected first or in or together with an ablative solution could reduce or eliminate the pain associated with a denervation procedure.

For use in renal sympathetic nerve ablation and nerve activity verification, the manually expandable ("push") guide tube embodiment of the PNASC would be used with the following steps (although not every step is essential and steps may be simplified or modified as will be appreciated by those of skill in the art):

1. Sedate the patient using standard techniques for cardiac or renal catheterization or septal ablation, for example—in a manner similar to an alcohol septal ablation, (Versed and narcotic analgesic).
2. Engage a first renal artery with a guiding catheter placed through the femoral or radial artery using standard arterial access methods.
3. Attach the nerve sensing electronics unit to the proximal ends of the wires attached to the distal sensors that will be used to sense nerve activity.
4. Flush the injection lumen with the ablative fluid (e.g. ethanol) or saline.
5. Flush flushing all the lumens of the PNASC but the injection lumen with saline.
6. Advance the distal end of the PNASC into the proximal end of the guiding catheter.
7. Advance the distal portion of the PSNAC through and beyond the distal end of the guiding catheter, until the radiopaque markers on the distal portion show that the distal portion of the PSNAC is at the desired location in the renal artery.
8. Manually advance the guide tubes outwardly from the body of the PNASC using the mechanism in the proximal section of the PSNAC until the guide tubes are fully expanded against the interior wall of the target vessel. Expansion can be confirmed by visualization of the radiopaque markers on the distal portions of the guide tubes.
9. Next, the injection tubes/needles are advanced coaxially through the guide tubes to penetrate through the internal elastic lamina (IEL) and media of the artery, then through the external elastic lamina (EEL) to a preset distance (typically between 2 to 10 mm but preferably about 2-6 mm) beyond the IEL into the mid to outer adventitial and/or peri-adventitial layer(s) of the vessel wall of the renal artery. The injection tubes/needles are thereby positioned to deliver the neuroablative agent(s) at or "deep to" (outside of) the adventitial plane. The depth of 2-6 mm deep relative to the IEL will minimize intimal and medial renal artery injury. The normal thickness of the media in a renal artery is between 0.5 and 0.8 mm while the sympathetic nerves can be as deep as 10 mm or deeper to the IEL. The depth limitation feature of the embodiments disclosed in the present disclosure has the distal opening of the needles set to be a fixed distance beyond the distal end of the guide tubes. In a normal renal artery the guide tubes would be positioned against the intimal wall. If there is intimal thickening from plaque or neointimal hyperplasia within the artery as seen by angiography, IVUS or OCT, then as much as 3-8 mm of penetration depth beyond the end of the end of the guide tube may be needed. Specific product codes (i.e., preset designs) with preset greater penetration depths or user available adjustments in the handle of the PSNAC are envisioned to facilitate this. If the vessel has a stenosis, it would be preferable to pick the site for needle penetration away from the stenosis and to treat the stenosis as needed with Percutaneous Coronary Intervention (PCI).
10. Measure the nerve activity from the sensors at or near the distal ends of the injection needles as a baseline (control) for comparison with the measurements of nerve activity following the ablation procedure.
11. Inject an appropriate volume of the ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or any other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1-3.0 ml. RF energy could also be applied to the needles to create a thermal denervation effect. This should produce a multiplicity of ablation zones (one for each injector tube/needle) that will intersect to form an ablative ring around the circumference of the target vessel. For ethanol the ideal injection would be between 0.15 and 0.6 ml with 0.3 ml being the standard dose. Contrast could be added to the injection either during a test injection before the neuroablative agent or during the therapeutic injection to allow x-ray visualization of the ablation zone. With ethanol, as an ablative agent, a volume of less than 0.6 ml is sufficient for this infusion as it will not only completely fill the needed volume including the sympathetic nerves, but is small enough that if accidentally discharged into the renal artery, would not harm the patient's kidneys.

12. Wait a period of time between 3 and 20 minutes and re-measure the nerve activity. If the activity has not decreased to a specified target for nerve activity reduction (either quantitatively or qualitatively), additional ablative fluid and/or thermal energy can be applied.
13. Retract the PNASC injector tubes/needles back inside the guide tubes.
14. Retract the guide tubes back into the tubular shafts of the PNASC.
15. The same methods as per prior steps can be repeated to ablate tissue and confirm the reduction in neural activity in the opposite (contra-lateral) renal artery.
16. Remove the PNASC from the guiding catheter completely.
17. Remove all remaining apparatus from the body.

It is also envisioned that the injection of a local anesthetic as disclosed in step 11, can be at the primary site of injection of ablative fluid, distal or proximal to the primary site. Similarly, the PNASC could be used with an energy delivery renal denervation device to both measure nerve activity and inject a local anesthetic. This technique can also apply to devices such as the PTAC of Fischell application Ser. No. 13/752,062 which can inject ablative fluid but does not have nerve sensing electrodes.

If the SNSC catheter is to be used to measure nerve activity during a renal denervation procedure, the method of use may include the following steps:
1. Sedate the patient using standard techniques.
2. Engage a first renal artery with a guiding catheter placed through the femoral or radial artery using standard arterial access methods with the distal end of the guiding catheter being situated beyond the ostium of the renal artery.
3. Introduce the distal end of the SNSC attached at its proximal end to its electronics control box through the guiding catheter into the renal artery to the desired site of neural ablation.
4. Expand the guide tube and sharpened wires/needles with distal sensors until the distal ends of the sharpened wires lie 2 to 10 mm beyond the IEL.
5. Measure the nerve activity of the sympathetic nerves and remove the SNAC from the body.
6. Retract the wires/needles and then the guide tubes and remove the SNSC from the body.
7. Perform the renal denervation procedure using chemical or energy based catheters.
8. Remove the renal denervation catheter from the body
9. Wait a preset period of time between 3 and 20 minutes.
10. Re-insert the SNSC and once again deploy the sharpened wires/needles with distal sensors into the periadventitial space.
11. Measure the nerve activity and compare to a preset level of reduction that would indicate success. If successful, retract the SNSC into the guiding catheter and do steps 4 through 10 in the other artery.
12. If there appears to be inadequate ablation. Remove the SNSC and reintroduce the renal denervation catheter to provide additional nerve ablation, and repeat nerve activity measurements again, as needed.
13. If desired, move the guiding catheter to the opposite (contra-lateral) renal artery.
14. Repeat steps 4 through 11.
15. Remove all remaining apparatus from the body.

There are numerous articles describing methods of measurement of nerve activity but for this application, external equipment may be provided that would include a digital read out of one or more electrical characteristics such as the peak voltage, average voltage, peak power and/or average power. The difference in measurements before and after the renal derivation procedure would indicate the effectiveness of the procedure. Of these average voltage would be the preferred measurement. The external equipment could also include a graphical display of the actual signal as well as means to select which pair of electrodes is being displayed. For example, a switch to choose electrodes 1-2, 2-3 or 3-1 would be desirable.

Similar to the PTAC designs disclosed by Fischell et al in U.S. patent application Ser. No. 13/752,062, both PNASC and SNSC embodiments of the present application, include the means to limit needle/wire penetration of the vessel wall in the proximal portion of the catheter. A handle or handles similar to that shown in FIG. 11 of the Fischell PTAC disclosure, are envisioned that would be used by the operator to cause first the expansion of the guide tubes and second, the advancement of the injection needles/wires. The reverse motion of these mechanisms would then retract the needles/wires back into the guide tubes and then retract the guide tubes back into the catheter body or under a sheath. Fischell et al in additional U.S. patent application Ser. Nos. 13/643,070, 13/643,066 and 13/643,065 describe such control mechanisms for advancing and retracting distal structures such as sheaths, guide tubes and injector tubes with distal injection needles. Interlocks and locking mechanisms to prevent accidental movement out of sequence of these mechanisms are also described and would be incorporated into the SNSC and PNASC embodiments of this disclosure.

Similarly, Fischell et al describe the proximal section with ports for flushing and ablative fluid injection. The embodiments disclosed in the present application can have similar structures and controls in the proximal section. The mid-section of the catheter would typically be three concentric tubes. In the manually expandable embodiment of the SNSC and PNASC embodiments disclosed herein, there is an outer tube that forms the main body of the catheter. A middle tube controls the advancement and retraction of the guide tubes and an inner tube controls the advancement and retraction of the wires (SNSC) or injector tubes with distal injection needles (PNASC). For the PNASC, the lumen of the inner tube is also the lumen that carries the ablative fluid injected in the injection port in the proximal section of the PNASC to the lumens of the injector tubes and injection needles and finally out though the distal opening at or near the distal ends of the injection needles. For the SNSC the inner tube provides control for advancement and retraction of the electrodes/sensors but is not used for injection of ablative fluids.

For both PNASC and SNSC, conducting insulated wires (which includes any electrically conductive elements for conducting a signal between the sensor and proximal end of the catheter) would run to the distal portion of the catheter, typically through the lumen of the inner tube. The PNASC would have radiopaque markers to show under fluoroscopy the extension of the needles through the artery wall into the periadventitial space. The SNSC would also have radiopaque markers on the sharpened wires to show under fluoroscopy the extension of the wires through the artery wall into the periadventitial space. In both PNASC and SNSC, the sensor itself would likely be made of gold or platinum and serve as a radiopaque marker.

Another important feature of the presently disclosed PNASC disclosed by Fischell in patent application Ser. No. 13/752,062 is a design that reduces the internal volume of the injection lumens of the catheter (the "dead space"). It is anticipated that less than 0.5 ml of an ablative fluid such as ethanol will be needed to perform Peri-Vascular Renal Denervation (PVRD). The dead space should be less than 0.5 ml and ideally less than 0.2 ml. With certain design features it is conceived that the dead space can be reduced to less than 0.1 ml. Running the insulated wires attached to each distal sensor actually will improve this further as the wires will take up volume in the injection lumens of the PNASC. Such features include using a small diameter<0.5 mm ID hypotube for the inner tube used for fluid injection for the PNASC, and/or designing the proximal injection port and or injection manifold at the proximal end of the PNASC to have low volume by having small <0.5 mm inner diameter and a short, <2 cm length.

In both the PNASC and SNSC devices, a wire attached to each distal sensor extends the entire length of the catheter and exits at or near the proximal end where the wires through a connector attach to an electronics module with a nerve activity display. The electronics module would include amplifiers for each sensor, analog-to-digital converters to digitize the signals and a central processing unit with memory (CPU) to process the signals and drive the nerve activity display. The electronics module can be very complex allowing each pair of sensors to be looked at and actual measurements of nerve activity displayed or it could be as simple as a 5 LED display for each sensor compared to the common ground with a calibrate button to normalize the level during initial measurement of sympathetic nerve activity. This would then light up all 5 LEDs showing maximum activity. Following the renal denervation procedure, the measurement would be taken again and the reduction in nerve activity would be displayed by illumination of the new level compared to the normalized value.

For example, if the post denervation level is 40% of the normalized level for one of the sensors, then only 2 of the 5 LEDs would be lit showing a 60% drop in nerve activity. An example of even simpler version would have a green, yellow and red LED for each sensor where green indicates nerve activity, yellow partial reduction and red significant reduction. A more complex version could use the baseline control activity and take an average activity over a specified measurement time, then compare the activity over a similar duration of nerve activity measurement and display a quantitative, numerical reduction value (e.g., "Nerve activity reduced by 64% compared to baseline nerve activity.")

As with many of the prior Fischell et al applications, it is an important feature for certain embodiments of this invention that the guide tubes are needle guiding elements for the advancement of the ultra-thin injection needles or sharpened wires that are advanced outwardly through the wall of the renal artery. Specifically, prior art such as Jacobson that describes curved needles that are advanced outwardly from a central catheter to penetrate the interior wall of a target vessel, have bare needles that are advanced on their own from the distal end or the side of a catheter. Without additional guiding (support) during advancement, needles that are thin enough to not cause blood loss following withdrawal from the wall of the artery are generally too flimsy to reliably penetrate as desired into the vessel wall.

Thus it is envisioned that a key aspect of the small needle embodiments disclosed in the present application is the inclusion of needle guiding elements such as guide tubes that allow the ultra-thin injection needles to be reliably advanced into the wall of a target vessel to the desired depth. Such guiding elements need not be a tube or have a round cross-section, they could be a half or partial tube, they can be a structure with a slot that provides a guide for the advance-able needles, and a guiding structure could be any expandable structure such as a spring that expands outwardly and provides radial support and a guide for the needles. The terms "expand" and "expands" are intended to refer to motion of a structure from a first position relatively closer to a longitudinal axis of the catheter to at least a second position that is relatively farther away from the longitudinal axis, whether the motion is by expansion, deflection, pivoting, or other mechanism. It is desirable that the needle guiding elements expand outwardly from the central catheter.

What is also included in the present application is the use of additional structures to provide radial and lateral support for the needle guiding elements as disclosed by Fischell in U.S. patent application Ser. No. 13/752,062. This is desirable if one seeks a uniform penetration and angular spread of the multiple needles. In addition, as the needles are advanced, and guided by the "guiding elements," (e.g., the guide tubes) the guiding element can, if unsupported, back away from the desired position against the interior wall of the vessel. For this reason, the present disclosure like the PTAC of Fischell includes the design of structures that provide radial ("backup") support for the needle guiding elements that provide resistance to the guiding elements backing away from the interior surface as the needles are advanced into the wall of the vessel.

There are other medical conditions which may be adversely affected by inappropriate (intrinsic) neurological activity. Early studies suggest that those patients who have undergone renal denervation (with radiofrequency ablation from inside the renal artery) may have improved diabetes and even decreased apnea episodes (in those that have underlying Obstructive Sleep Apnea). The embodiment of the present invention ablation device (PNASC) will offer more selective and complete ablation. We believe that with the addition of the sensing characteristics of the catheter that we will be able to tailor the therapy to the desired neuro-modulated response.

Another potential application of the PNASC applies to COPD (Chronic Obstructive Pulmonary Disease) that has a potentially reversible component often treated with sympathomimetic agents and also those that decrease (atropine like) parasympathetic tone. Current medical therapy has significant side effects because of the systemic effects of these medications. Use of the PNASC (or PTAC of Fischell et al Ser. No. 13/752,062) to provide focal ablation of parasympathetic system and/or augmentation of the sympathetic system may allow these patients improved pulmonary function without and with fewer oral or inhaled medications.

Thus a feature of the present application is to have a Sympathetic Nerve Sensing Catheter (SNSC) that is percutaneously delivered with outwardly expandable sensors designed to penetrate through the renal artery wall into the periadventitial space where the sensors can be used with associated external electronics to measure sympathetic nerve activity, including changes in the level of sympathetic nerve activity following a renal denervation procedure. Such an SNSC could be used with any renal denervation system or device.

Thus a feature of the presently disclosed Perivascular Nerve Ablation and Sensing Catheter (PNASC) is to have a percutaneously delivered catheter with expandable supported needle guiding elements through which injection needles are advanced for injection of an ablative fluid into or beyond the outer layers of the renal artery with sensing electrodes and associated external electronics to measure sympathetic nerve activity, including changes in the level of sympathetic nerve activity following a renal denervation procedure.

Another aspect of the present application is to have an electronics module external to the PNASC or SNSC which amplifies the signal from the distal sensors located in the periadventitial space and provides a display of nerve activity to allow the user to identify the effectiveness of the renal denervation procedure.

Still another aspect of the present disclosure is to have at least three guide tubes/needle guiding elements in the PNASC each having a radiopaque marker. The guide tubes/needle guiding elements being manually expandable outwardly from within a set of tubular shafts which provide additional support and backup to stabilize each guide tube/needle guiding element against the interior wall of the target vessel. Expansion of the guide tubes/needle guiding elements is accomplished by manipulation of a mechanism in the proximal portion of the catheter.

Yet another aspect of the SNSC and PNASC of the present disclosure is to include one or more of the following radiopaque markers to assist in positioning, opening, closing and using the PNASC. These include the following:

A radiopaque ring marking the distal end of the outer tube;

Radiopaque markers at, or very close to the ends of the guide tubes using either metal bands or plastic with a radiopaque filler such as barium or tungsten;

Radiopaque markers on the distal portion of the injection needles or sharpened wires;

Radiopaque wires inside the lumen of the injector tubes and/or injection needles;

Wires of radiopaque metals such as gold or platinum to conduct the signals from the distal sensors to the electronics module.

Making the sympathetic nerve sensing electrodes of a radiopaque material such gold or platinum.

The distal fixed guide wire of the PNASC being radiopaque (e.g., using platinum wire);

There is provided in accordance with one aspect of the present invention, a catheter for sensing the activity of nerves outside of the interior wall of a target vessel of the human body. The catheter comprises a catheter body, having a central axis extending in a longitudinal direction and also having a central lumen. At least two needle guiding elements are provided, and adapted to expand outwardly toward the interior wall of the target vessel. At least two needles, each needle having a distal electrode, are adapted to be advanced outwardly guided by the at least two needles guiding elements, to penetrate the interior wall of the target vessel and advance further into the tissue outside of the inside wall of the target vessel. At least two wires are provided for conducting signals sensed by at least two electrodes, the wires connecting the electrodes to external equipment outside of the catheter.

In one implementation of the invention, each needle guiding element is a guide tube, having a lumen, for receiving a needle therethrough. The catheter may include at least three needle guiding elements, three needles, and three insulated wires.

In one implementation of the invention, the needle guiding elements have a curved distal portion with a first radius of curvature, and the needles have a curved distal portion with a second radius of curvature. The first and second radius of curvature are preset to be within about 25%, and in some embodiments no more than about 15%, and in one embodiment no more than about 5% of each other in an unconstrained expansion.

In accordance with another aspect of the invention, there is provided a catheter for sensing the electrical activity of extravascular tissue at a target site. The catheter comprises an elongate flexible body, and at least one flexible extendable arm having a sharpened tissue penetrating tip carried by the body. The extendable arm is movable between a first position in which the tip is positioned within the body and a second position in which the tip is displaced radially outwardly from the body to penetrate tissue and reach the target site. An electrode is carried by the extendable arm, and an electrical conductor extends through the body and is in electrical communication with the electrode.

In one embodiment of the, the catheter comprises three flexible extendable arms. Preferably, a needle support element in the form of a support tube or guide tube is provided for each flexible extendable arm. The support tubes are movable between a first position within the body and a second position extending away from the body. The flexible extendable arms are movable through the support tubes.

In accordance with a further aspect of the present invention, there is provided a dual purpose catheter for both disrupting and evaluating the electrical conductivity of a nerve. The disruption function is provided by application of electrical voltages between at least one pair of electrodes. Such voltages can produce electroshock, electrocautery or RF ablation depending on the intensity and frequency of the voltage and the material and structure of the electrodes.

The dual purpose catheter comprises an elongate flexible body, and at least two tissue penetrating probes extendable laterally from the body. A fluid effluent port is provided on each probe, each fluid effluent port in fluid communication with a fluid supply lumen extending through the body. An electrode is carried by each probe, each electrode in electrical communication with a unique conductor extending through the body. Preferably, each tissue penetrating probe is movably advanceable through a tubular support.

In accordance with a further aspect of the present invention, there is provided a method of evaluating a nerve in a patient. The method comprises the steps of providing a catheter having an elongate flexible body with a proximal end, a distal end and a first electrode carried by the distal end. The first electrode is movable between a retracted position within the catheter and an extended position for piercing a vessel wall.

The distal end of the catheter is positioned at an intravascular site within the patient. The first electrode is advanced into the wall of the vessel, and an electrical characteristic of the nerve is measured. The measuring step may include placing the first electrode and a second electrode into electrical communication with an instrument electrically coupled to the proximal end of the catheter. The second electrode may be carried by the catheter, or may be in contact with the patient's skin.

There is provided in accordance with a further aspect of the present invention a catheter system for energy based renal denervation from two or more electrodes that are placed deep to (radially outside of) the location of the pain nerves of the renal artery so as to ablate the sympathetic nerves while reducing the pain to the patient as compared with energy based denervation from inside of the renal artery.

There is provided in accordance with a further aspect of the present invention a catheter system for sensing nerve activity in the volume of tissue just outside of the vessel of the human body. The catheter system comprises electronic equipment designed to measure nerve activity, a first electrode, and a second electrode. The second electrode may be incorporated near the distal end of the catheter, the catheter including a mechanism to position the distal electrode into the volume of tissue outside of the inside wall of a vessel of the human body. The position of the electrode may be selected from the outer layer of the vessel, or the volume of tissue outside of the outer layer of the vessel. Conductive wires are adapted to connect the first and second electrodes to the electronic equipment.

In accordance with other aspects of the invention, there are provided methods and devices for treatment of extravascular/perivascular tissue such as denervation of renal nerves, while minimizing pain to the patient. Pain associated with first generation RF renal denervation devices may be attributable to the nonspecific destruction of nerves associated with the vessel wall. Pain is believed to be associated with destruction of unmyelinated "C-fibers" which may run in or just outside of the media (smooth muscle layer) of the vessel or in or just outside of the external elastic lamina (outer skin of the media). The sympathetic nerve fibers that affect blood pressure are predominantly the "efferent" nerves that transmit signals from the brain to the kidney and back. These nerves are believed to run almost exclusively in or outside of the outer layer of the artery (the adventitia) and deep to (outside of the external elastic lamina. Conventional intravascular energy delivery by ultrasound or RF will ablate tissue from the endothelium (the inside layer) of the artery all the way to the adventitia, thus damaging both unmyelinated "C-fibers" as well as a portion of the sympathetic nerve fibers. Intravascular energy delivery may be limited in efficacy as it cannot damage the deeper sympathetic nerves outside of the adventitia without causing irreparable damage to the inner layers of the artery.

The current inventors have observed that patients treated with the devices of the present invention experienced essentially no pain during injection of ethanol into the adventitia (i.e., deep to the pain fibers) and believe that delivering ablative therapy generally (energy, chemical or other modalities) to the adventitia or outside of the adventitia while sparing the media and other intervening tissue will achieve a better therapeutic ablation with minimal or no pain.

Thus, one aspect of the present invention provides a catheter for preferentially denervating efferent nerves while sparing unmyelinated C-fibers adjacent a target vessel. The catheter comprises an elongate, flexible catheter body having a central axis extending in a longitudinal direction; at least two electrode guiding elements adapted to expand outwardly toward the interior wall of the target vessel; at least two electrodes, each electrode having a distal uninsulated electrode tip, the at least two electrodes adapted to be advanced outwardly, guided by the at least two electrode/needle guiding elements, to penetrate the interior wall of the target vessel and position the electrode tips beyond the external elastic lamina.

Preferably each electrode guiding element is a guide tube having a lumen. Each electrode may be advanced outwardly coaxially through the lumen of a guide tube. At least three electrode guiding elements and three electrodes may be provided.

A catheter for localized RF ablation of extravascular tissue at a target site while sparing adjacent endothelium, comprises an elongate, flexible body; at least one flexible extendable arm having an electrically conductive tip carried by the body of the catheter, the extendable arm movable between a first position in which the electrically conductive tip is positioned within the body of the catheter and a second position in which the tip is displaced radially outwardly from the body to penetrate tissue and reach the target site, such that the electrically conductive tip is positioned completely beyond the endothelium. The catheter may comprise at least three flexible extendable arms. A support tube movable between a first position within the body and a second position extending away from the body may be provided the flexible extendable arm extends through the support tube.

One method of the present invention comprises a method for preferentially denervating efferent nerves while sparing unmyelinated C-fibers adjacent a target vessel to treat hypertension while minimizing procedure discomfort, comprising the steps of providing a catheter having an elongate, flexible body with a proximal end, a distal end, and a first electrode carried by the distal end, the first electrode movable between a retracted position within the catheter and an extended position for piercing a vessel wall; positioning the distal end of the catheter at an intravascular site within the patient; advancing the first electrode into the vessel wall at a puncture site; and denervating tissue at a first depth deep to (outside of) the external elastic lamina to preferentially denervate efferent nerves while sparing unmyelinated C-fibers at a second depth near to or within the external elastic lamina, the second depth less than the first depth.

It is also envisioned that the method above can include using the electrodes to sense electrical activity from the efferent nerves before and after ablation to determine the effect of the ablation.

Another aspect of the method of minimizing pain during renal denervation, comprises the steps of advancing a distal end of a catheter translumenally to a site in a renal artery; advancing an ablation element from the catheter, through the media and into the adventitia; and ablating tissue within the adventitia while sparing the media. The ablation element may be an ablative fluid delivered from an effluent fluid port for delivery. Alternatively, the ablation element may be an energy delivery element including RadioFrequency (RF), microwave, cryogenic, ultrasound, electrocautery or heating element.

In any of the foregoing, the ablative element (e.g., conductive surface of an electrode; fluid from an effluent port)

is preferably carried by the catheter such that it can penetrate the vessel wall from inside of the vessel and position the ablative element to enable it to selectively ablate tissue at a depth of at least about 3 mm, preferably at least about 5 mm and in some embodiments at far as 10 mm into the vessel wall from the endothelium in the direction of the adventitia, so that it can ablate nerves in and outside of the adventitia minimizing damage to the nerves in or near the media. Preferably the catheter permits blood perfusion through the renal artery during the ablation and/or nerve activity sensing procedures.

An additional reason perivascular energy based ablation will be more effective than intravascular is that it is less damaging to the media that will be cooled by the significant blood flow through the artery, while there is much less cooling in the perivascular space.

These and other features and advantages of this invention will become obvious to a person of ordinary skill in this art upon reading of the detailed description of this invention including the associated drawings and the claims.

BRIEF DESCRIPTION OF THE DRAWINGS

FIG. 12 is a longitudinal cross section of another embodiment of the distal portion of the artery penetration portion of the SNSC.

FIG. 13 shows a modification of the distal portion of FIG. 12 that makes this design a PNASC with the addition of side holes for fluid injection into the perivascular space.

DETAILED DESCRIPTION OF THE DRAWINGS

Figure 1:
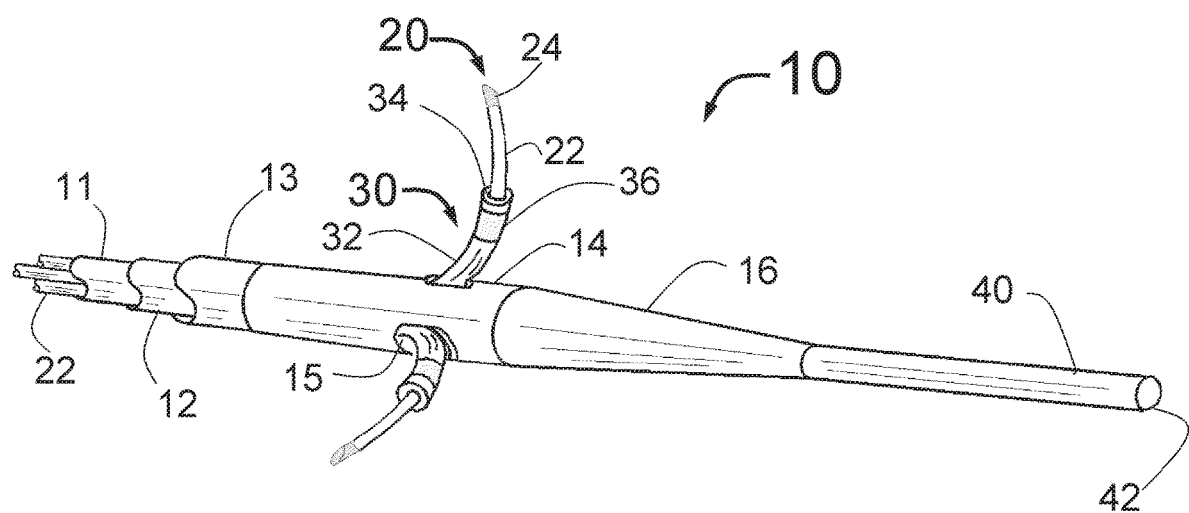
FIG. 1 is a schematic view of the distal portion of an SNSC which uses three expandable sharpened wires in its open position as it would be manually expanded for measurement the activity of the sympathetic nerves outside of the renal artery.

FIG. 1 is a schematic view of the distal portion of a SNSC 10 in its open position, showing an inner tube 11, middle tube 12, outer tube 13, outer tube extension 14 having distal openings 15 through which the guide tubes 30 with radiopaque markers 36, distal tip 34 and outer layer 32 are advanced outwardly from the body of the SNSC 10 through the openings 15 in the outer tube extension 14. Also shown is the tapered section 16 and fixed guide wire 40 with distal tip 42. The sharpened wires 20 with outer insulation 22, and core wire 24 are shown in their fully deployed positions. The wires 20 run all the way to and beyond the proximal end of the SNSC 10 and are shown here in the distal portion of the SNSC 10 as lying within the lumen of the inner tube 11. The insulation 22 has been removed from the distal portion of the wire 20 which will act as an electrode for sensing nerve activity.

The openings 15 support the guide tubes 30 as the guide tubes 30 are advanced outwardly before the advancement of the sharpened wires 20. The SNSC 10 of FIG. 1 has three guide tubes with the third tube hidden behind the catheter and not visible in this schematic view. Although the SNSC 10 of FIG. 1 has three guide tubes 30, it is envisioned that other embodiments could have as few as one or as many as eight guide tubes with an optimum number being three or four. A larger diameter target vessel might suggest the use of as many as 4 to 8 guide tubes 30 and sharpened wires 20. The term sensor and electrode will be used interchangeably here to describe a conducting electrical contact which forms the distal end of the sharpened wire 20. Such electrodes can be used in pairs to measure nerve activity or produce electrical or RF energy delivery. Ideally the electrode is made from or coated with a radiopaque material such as gold or platinum.

Different shapes are envisioned for the distal openings (or windows) 15 in the outer tube extension 14 where the guide tubes 30 exit. These possible shapes include a racetrack design with curved (e.g., round) proximal and distal ends and straight sides in the axial direction, and oval or round shapes. It is also envisioned that there could be a movable flap covering each opening 15 or a slit that could be opened to make the outer surface of the SNSC smooth for better delivery through a guiding catheter into the renal artery.

It is a feature of this invention that the guide tubes 30 are needle guiding elements for the ultra-thin sharpened wires 20. Specifically, prior art such as Jacobson that describe curved needles that are advanced outwardly from a central catheter to penetrate the wall of a target vessel, have needles that are advanced (naked) on their own from the distal end or side of a catheter. Without additional guiding and backup support during advancement, needles/sharpened wires that are thin enough to essentially eliminate the risk of bleeding following penetration and withdrawal from the wall of the artery are generally too flimsy to reliably penetrate as desired into the vessel wall. Thus it is envisioned that the SNSC 10 of the present application preferably includes needle-guiding elements such as the guide tubes 30 that allow the ultra-thin sharpened wires 20 to be reliably supported and advanced into the wall of a target vessel to the desired depth.

Figure 2:
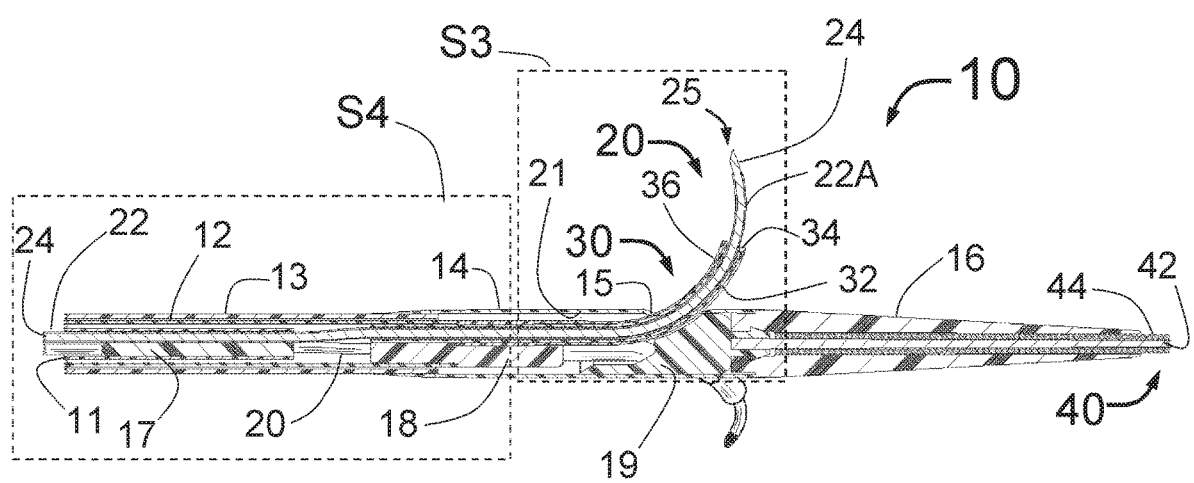
FIG. 2 is a longitudinal cross-section of a distal portion of the SNSC of FIG. 1 in its open position.
Figure 3:
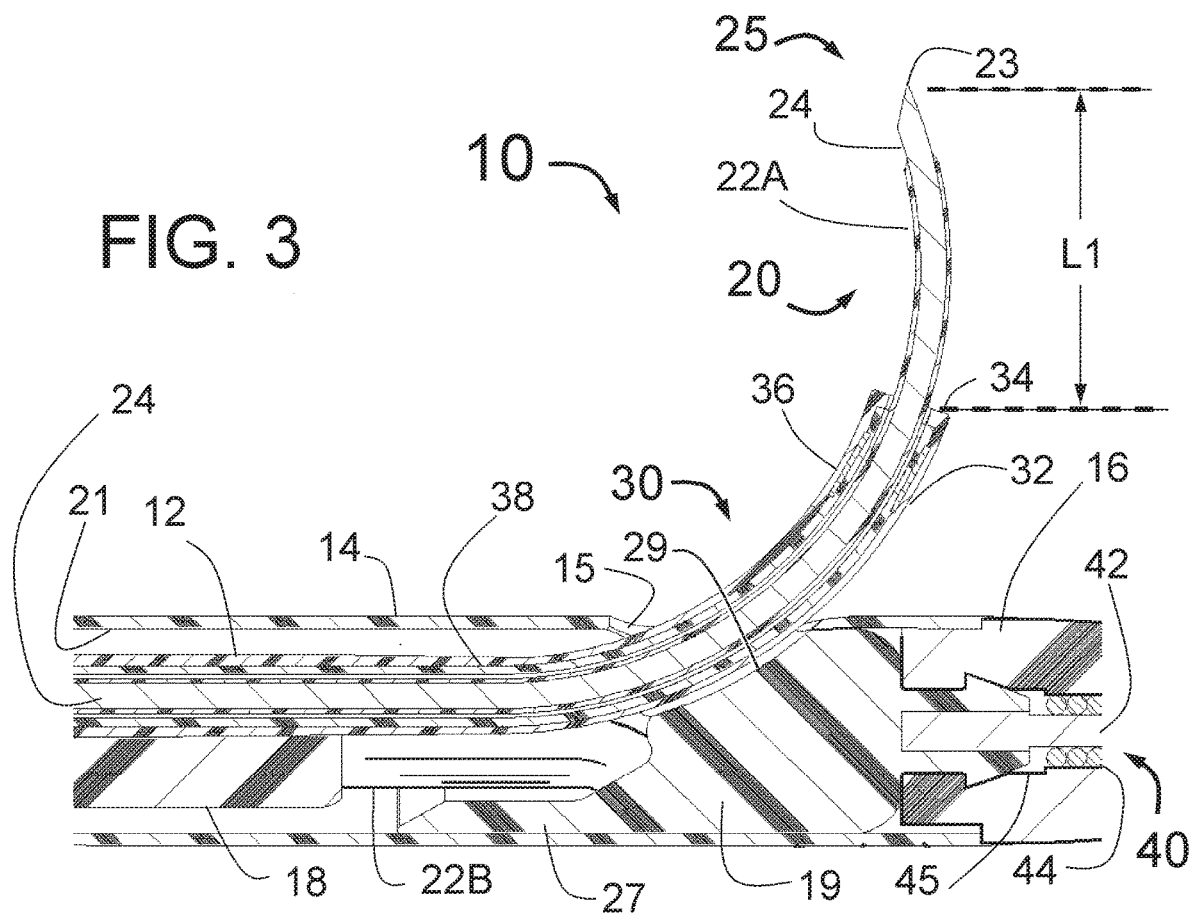
FIG. 3 is an enlargement of region S3 of the SNSC of FIG. 2.
Figure 4:
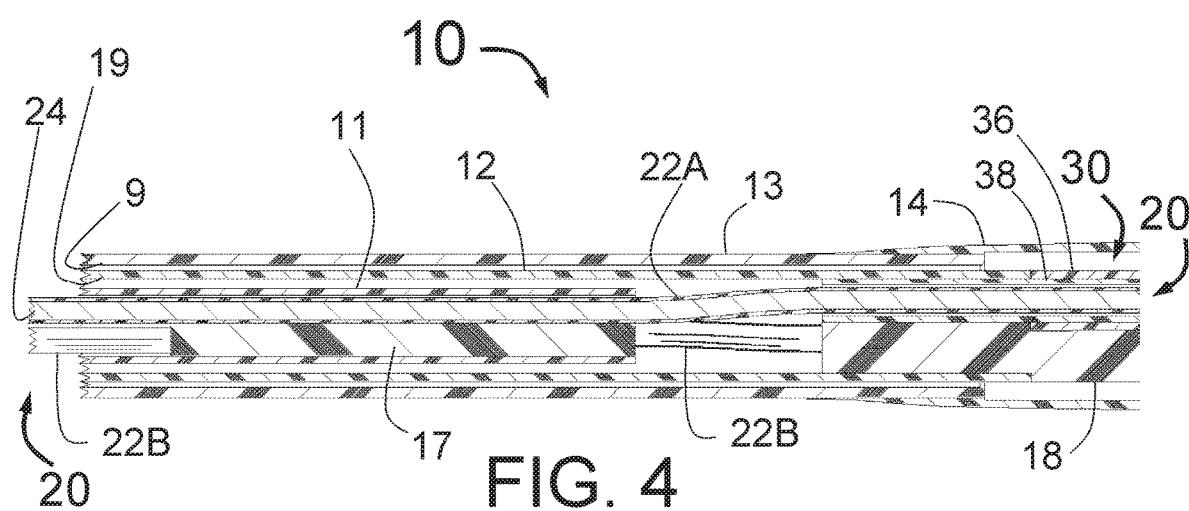
FIG. 4 is an enlargement of region S4 of the SNSC of FIG. 2.

FIG. 2 is a longitudinal cross-section of a distal portion of the SNSC 10 as shown in FIG. 1. The proximal end of FIG. 2 shows the three concentric tubes, the outer tube 13, middle tube 12 and inner tube 11 which form the central portion of the SNSC 10. The outer tube 13 is attached at its distal end to the outer tube extension 14 which is in turn attached to the tapered section 16. The fixed guide wire 40 with core wire 42 and outer layer 44 extends distally from the distal end of the tapered section 16. It should be noted that only part of the length of the guide wire is 40 shown in FIG. 2, its full length is shown in FIG. 1. Enlargements of the sections S3 and S4 of FIG. 2 are shown in FIGS. 3 and 4 respectively.

FIG. 2 shows the guide tube 30 with outer layer 32, distal tip 34 and radiopaque marker 36 in its fully deployed position as advanced through the opening 15 in the outer tube extension 14. The interior surface of the outer tube extension 14 forms part of the tubular shaft 21 which is preferably made from a stiff material such as a metal or high durometer plastic so that it will be relative rigid as the guide tubes 30 are advanced and retracted.

Coaxially within the lumen of the guide tube 30 is the insulated wire 20 with insulated outer layer 22A and core wire 24. The uninsulated distal portion of the wire 20 forms the electrode 25 which acts as a sensor that in combination with either or both of the other two electrodes 25 at the ends of the other two sharpened wires 20, or with a remote electrode in electrical communication with the patient, can be used to measure activity of the sympathetic nerves in the perivascular space outside of the renal artery.

Figure 5:
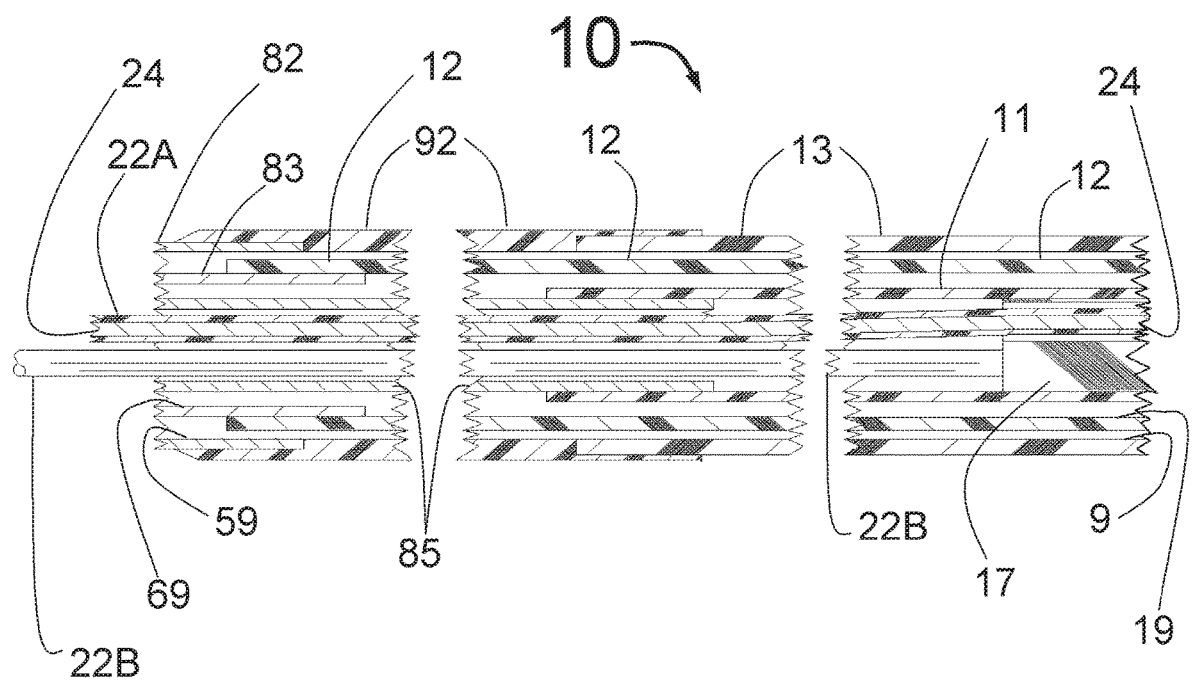
FIG. 5 is a longitudinal cross-section of the central portion of the SNSC showing the three proximal hypotubes.

The central portion of the SNSC 10 is shown in FIG. 5.

The central buttress 19 shown in FIG. 2, supports the guide tube 30 both as it is pushed distally and after it is fully deployed. This central buttress 19 also provides radial support for the advanced guide tubes 30 that prevents the guide tubes 30 from backing away from the interior wall of the target vessel as the sharpened wires 20 are advanced through the guide tubes 30 forward to their desired position in the periadventitial space 2-10 mm beyond the interior wall of the target vessel. Additional lateral support for the guide tube 30 is provided by the sides of the openings 15 that in combination with the central buttress 19 provide both radial and circumferential/lateral support both during guide tube 30 advancement and outwardly expansion as well as providing backup during delivery of the injection needles 20 through the interior wall of the target vessel. The buttress may comprise a deflection surface such as a curved or linear ramp, which may in a curved embodiment correspond to the radius of curvature of the outer surface of the guide tube 30.

Another feature of the SNSC 10 is that each sharpened wire 20 has a central axis with the same, or nearly the same, radius of curvature as the central axis of the corresponding guide tube 30 when measured in an unconstrained state. In addition, the length of the guide tubes 30 is preferably at least as long as the distal curved portion of the sharpened wires 20. This design constrains the curved portion of each sharpened wire 20 within the lumen of the guide tube 30 so that the sharpened wire 20 cannot twist or change position.

The distal portion of a design example of the central buttress 19 is shown in greater detail in FIG. 17 of U.S. patent application Ser. No. 13/752,062 by Fischell et al.

As seen in FIG. 2 the plastic cylinder 17 attaches the inner tube 11 to the three sharpened wires 20. The inner tube 11 and plastic cylinder 17 can slide along the longitudinal axis of the SNSC 10 inside of the middle tube 12 which is shown with uniform diameter over its length including the portion coaxially outside of the plastic cylinder 17.

FIG. 3 is the enlargement of section S3 of the longitudinal cross-section of the SNSC 10 as shown in FIG. 2. FIG. 3 shows the details of the guide tubes 30 with interior layer 38, outer layer 36, distal end 34 and radiopaque marker 32. Coaxially within the lumen of the guide tube 30 is the insulated wire 20 with insulated outer layer 22A and core wire 24 with sharpened needle tip 23. The uninsulated distal portion of the wire 20 forms the electrode 25 for sensing sympathetic nerve activity in the perivascular space outside of the renal artery. The other two of the three wires 20 have insulated layers 22B and 22C (not shown). Radiopacity of the tip of the sharpened wires 20 is important so that it can clearly be seen that the wire tips 23 are in the perivascular space. This can be accomplished by using a dense metal such as gold or platinum for the core wire 24 or by attaching a radiopaque marker at or near the tip 23. Plating the wire tip 23 with gold could also be effective.

The guide tubes 30 are advanced and retracted through the tubular shaft 21 with distal opening 15. The three guide tubes 30 are attached to each other near their proximal ends by the guide tube connector 18. FIG. 3 also clearly shows how the guide tube 30, when advanced against the central buttress 19 is forced outwardly and is supported by the curved ramp 29 of the central buttress 19 as well as the sides of the opening 15 of the tubular shaft 21. The central buttress 19 also has proximal fingers 27 that provide additional lateral support for the guide tubes 30.

The outer tube extension 14 connects at its distal end to the tapered section 16 which in turn lies coaxially around the guide wire 40 with core wire 42 and outer layer 44.

Figure 16:
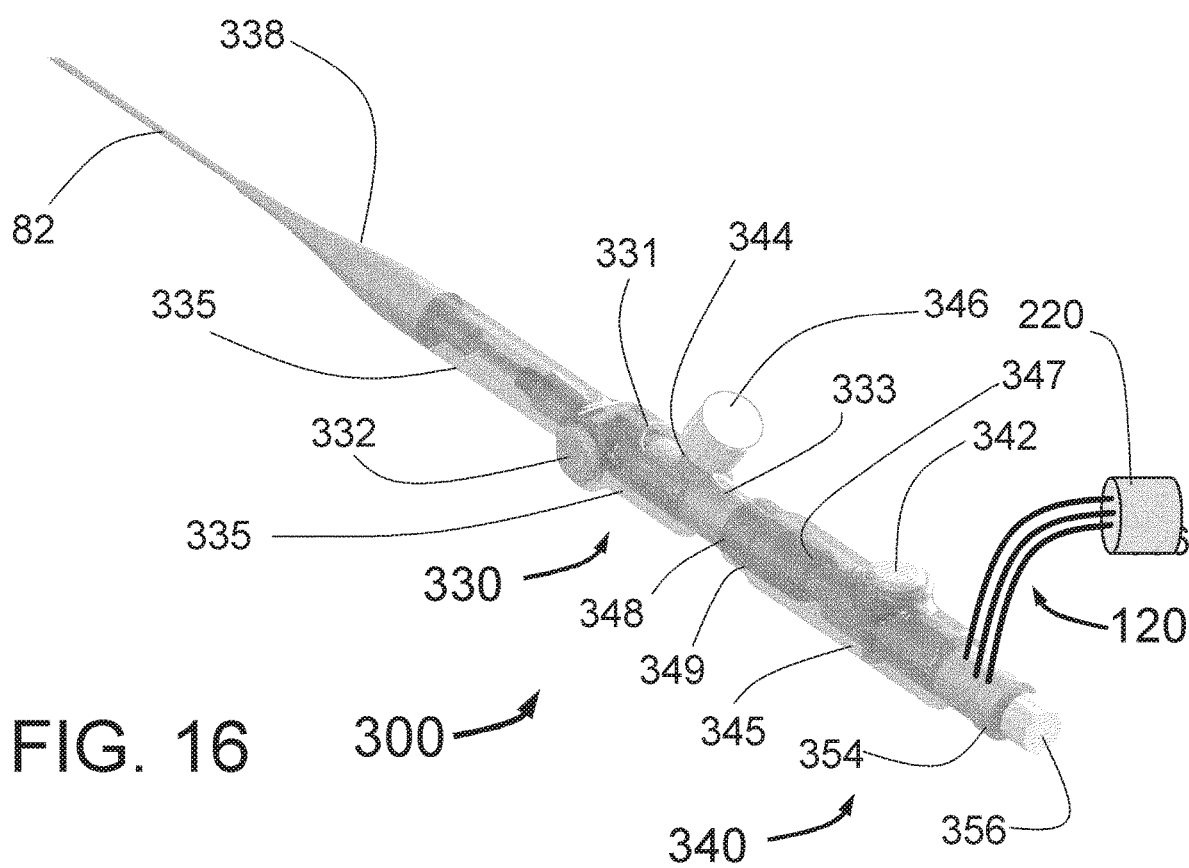
FIG. 16 is a schematic view of the mechanisms at the proximal portion of the SNSC/PNASC.

Also shown in FIG. 3 is the penetration depth L1 which is the distance from the distal end of the guide tube 34 to the distal end 23 of the core wire 24. Mechanisms at the proximal section of the SNSC 10 (as shown in FIG. 16) control the motion of the distal components of the SNSC 100 including the guide tube 30 and the sharpened wires 20. In one embodiment, the proximal section also includes the mechanisms to limit and/or adjust the penetration depth L1 of the distal end 23 of the sharpened wires 20.

It is envisioned that the central buttress 19 and distal openings 15 can, as shown in FIG. 3, be separate components of the SNSC 10 or they can be formed as a single molded or machined part as is shown in FIG. 17 of Fischell et al Ser. No. 13/752,062. The distal tip 45 of the central buttress 19 provides the attachment to secure the buttress 19 to the tapered section 16. Additionally, 19, 15 and 16 could be a single component molded or machined.

While the preferred embodiment of the SNSC 10 has the guide tubes 30 with a pre-formed curved shape, flexible naturally straight guide tubes are also envisioned where the buttress 19 forces the straight guide tubes to curve outwardly against the interior wall of the target vessel.

While the term "central buttress" will be used herein, the key component of the buttress 19 is the deflection surface such as ramp 29 that provides radial and some lateral support for the deployed guide tubes 30. Specifically, the curved ramp 29 of the buttress 19 supports and guides the outward motion of the guide tubes 30 as they exit though the distal openings 15 and also provide radial support for the guide tubes 30 and sharpened wires 20, as they come into contact with (engage) the interior wall of the target vessel. Additional lateral support is provided by the fingers 27 of the central buttress 19 and the sides of the tubular shaft 21 and sides of the openings 15. Such lateral support ensures that the guide tubes move radially outward without deflections in the circumferential (transverse to the longitudinal axis of the catheter) direction.

While the central buttress 19 shown in FIG. 3 is a plastic part, a radiopaque metal part, such as stainless steel, or a plastic material that includes radiopaque filler such as tungsten could be advantageously employed for showing the exact location where the guide tubes 30 will exit the SNSC 10. It is also envisioned that a radiopaque marker could be placed or attached to a portion of the openings 15 or buttress 19 or outer tube extension 14 to show the likely spot where the guide tubes 30 and thus the sharpened wires 20 would engage the interior wall of the target vessel.

Many of the components of the SNSC 10 are typically made from plastic materials such as polyamide, polyurethane, nylon or tecothane. These include the outer tube 13, middle tube 12 and inner tube 11, the outer tube extension 14, inner layer 38 and outer layer 36 of the guide tubes 30, the tapered section 16, the buttress 19, the guide tube connector 18 and the plastic cylinder 17. The plastic cylinder 17 can be a molded part or be epoxy or another resin that is injected to glue the wires 20 together within the lumen of the inner tube 11.

It is also envisioned that any or all of the inner tube 11, middle tube 12 or outer tube 13 could also be a metal hypotube or a metal reinforced plastic tube.

The wires 20 would typically be made of a springy or shape memory metal such as nitinol or a denser metal such as the cobalt chromium alloy L605. It is also envisioned that to enhance radiopacity, the uninsulated distal end could be plated in gold or other radiopaque material. Another way could be to have a gold cap attached to the distal end of the core wire 24. The insulated layers 22A, 22B and 22C are of a plastic material. The guide tube 30 radiopaque marker 32 could be made of a radiopaque material such as gold, platinum or tantalum or an alloy of these or similar metals. The core wire 42 of the fixed guide wire 40 would typically be stainless steel and the outer layer 44 would be wrapped platinum or platinum iridium wire. The outer layer could also be a polymeric material. Any or certain portions of the outside of the SNSC 10 could be lubricity coated to provide improved performance. The sharpened wires 20 should be smaller than 0.5 mm in diameter and preferably less than 0.3 mm in diameter to avoid any blood loss or leakage as the wires 20 penetrate into the wall of the target vessel and are then removed.

FIG. 4 is the enlargement of section S4 of FIG. 2 showing the transition from the central portion to the distal portion of the SNSC 10 including the outer tube 13, middle tube 12 and inner tube 11. Also shown is the connection between the outer tube 13 and the outer tube extension 14.

The guide tube connector 18 connects the three guide tubes 30 to the middle tube 12 that provides the impetus for advancement and retraction of the three guide tubes 30. The motion of the middle tube 12 is produced by the motion of control mechanisms at the proximal end of the SNSC 10. The plastic cylinder 17 lies inside of the distal portion of the inner tube 11 and connects together the three sharpened wires 20 with core wires 24 and insulated layers 22A, 22B and 22C (not shown), so that advancement and retraction of the inner tube 11 provides simultaneous advancement and retraction of the wires 20. Also shown in FIG. 4 are the flushing spaces between the several tubes. Specifically shown is the outer annular space 9 between the middle tube 12 and the outer tube 13 and the inner annular space 19 between the inner tube 11 and the middle tube 12. Each of these spaces 9 and 19 are to be flushed through with normal saline solution prior to insertion of the SNSC 10 into the patient's body.

FIG. 4 also shows how the wire 20 with insulating layer 22A extends from the distal end of the plastic cylinder 17 inside the distal end of the inner tube 11 and then enters the lumen of the inner layer 38 of the guide tube 30 at the proximal end of the guide tube 30. The guide tubes 30 and guide tube connector 18 are attached coaxially within the distal section of the middle tube 12. Thus longitudinal motion of the middle tube 12 will cause longitudinal motion of the guide tube connector 18 and guide tubes 30 thus allowing the mechanism at the proximal section of the SNSC 10 to advance and retract the guide tubes 50 with respect to the outer tube 13 and outer tube extension 14.

The penetration depth limitation could be a mechanism that limits the forward motion of the distal end of the inner tube 11 with respect to the guide tube connector 18. A ring or other structure situated between the distal end of the inner tube 11 or plastic cylinder 17 and the proximal end of the guide tube connector 18 would limit the forward (distal) motion of the distal end of the inner tube 11 and thus limit penetration of the wires 20 beyond the distal ends 34 of the guide tubes 30. Such a structure could be unattached, or attached to an internal structure of the SNSC 10 shown in FIG. 4 such as the inner tube 11, plastic cylinder 17, wires 20, guide tube connector 18, proximal ends of the guide tubes 30 or the middle tube 12. Such a structure could also have a length adjustment such as screw threads that would allow it to be used to calibrate the penetration depth L1 of the wires 20 beyond the distal ends 34 of the guide tubes 30. It should be noted that the structure of the SNSC 10 shown in FIG. 4 is similar to that of FIG. 5 of Fischell et al application Ser. No. 13/752,062. While Fischell shows transverse cross sections for clarity they will not be shown here as they are nearly identical except that the injector tubes with a platinum core wire are now solid insulted wires 20.

Fischell et al Ser. No. 13/752,062 in FIGS. 8-11 also shows a set of schematic views that illustrate how the PTAC 100 is used for peri-vascular renal denervation. The same schematic views are applicable here with sharpened wires 20 replacing the injector tubes with sharpened distal needles of Fischell.

FIG. 5 illustrates longitudinal cross-sections of three central portions of the SNSC 10 of FIGS. 1 through 4. At the proximal end of the central portion of the SNSC 10 are three concentric metal hypotubes, an outer hypotube 82, middle hypotube 83 and inner hypotube 85. These are typically made from thin walled metallic tubing such as stainless steel, L605, cobalt chromium or nitinol. The outer hypotube 82 of the SNSC 10 attaches at its distal end to a proximal plastic outer tube 92 typically made from a relatively high durometer plastic, for example polyimide. As seen in the central cross-section of FIG. 5, the proximal plastic tube 92 attaches at its distal end to the proximal end of the outer tube 13 also shown in FIGS. 1 through 4. The outer tube 13 is typically made from a lower durometer/more flexible plastic than the proximal plastic tube 92.

As shown in the proximal section of FIG. 5, the middle hypotube 83 is attached at its distal end to the middle tube 12. As shown in the central section of FIG. 5 the inner hypotube 85 is attached at its distal end to the proximal end of the inner tube 11.

Also shown in distal section of FIG. 5 is the plastic cylinder 17 that connects the inner tube 11 to the wires 20 as shown in FIG. 4.

Figure 6:
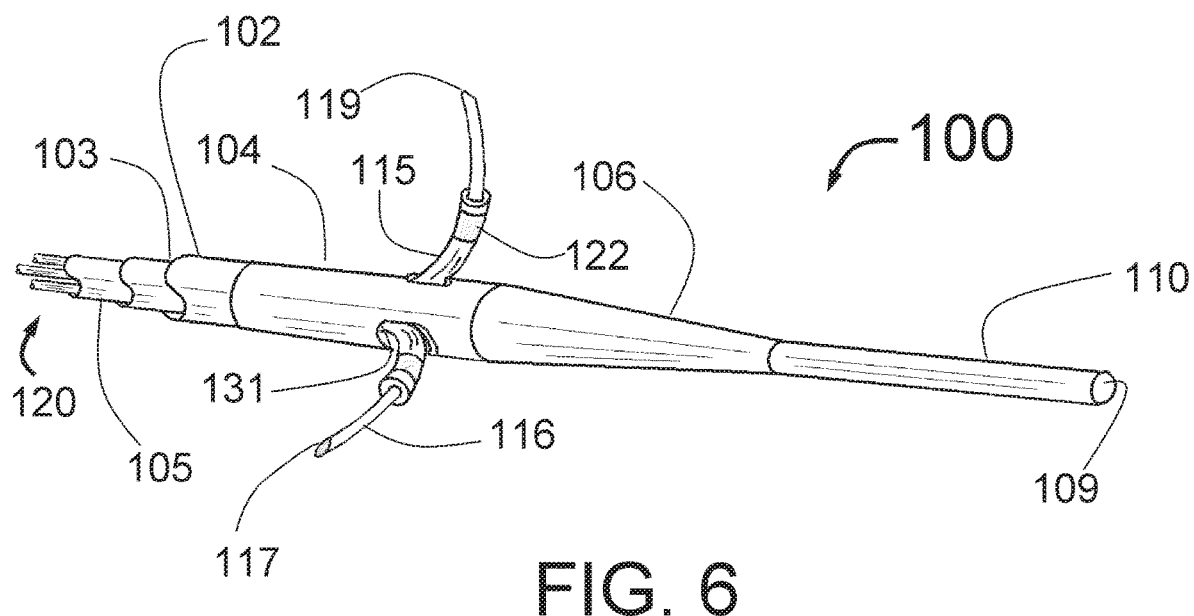
FIG. 6 is a schematic view of the distal portion of an SNSC or PNASC which uses three expandable NITINOL tubes with distal electrodes that act as sensors for nerve activity. The view shows the SNSC or PNASC in the open position following manual expansion that places the sensors in the periadventitial space to allow measurement the activity of the sympathetic nerves outside of the renal artery.

FIG. 6 is a schematic view of the distal portion of a SNSC 100 in its open position, showing an inner tube 105, middle tube 103, outer tube 102, outer tube extension 104 having distal openings 131 through which the guide tubes 115 with radiopaque markers 122 are advanced outwardly from the body of the SNSC 100. Also shown is the tapered section 106 and fixed guide wire 110 with distal tip 109. The signal wires 120 which connect to the electrodes 117 carry the signals sensed by the electrodes to an electronics module for monitoring and measuring the activity of the sympathetic nerves.

The sensor tubes 116 with distal sharpened sensing needles 119 and sensing electrode 117 are shown in their fully deployed positions. The openings 131 support the sides of the guide tubes 115 as the guide tubes 115 are advanced outward before the advancement of the sensor tubes 116 with distal sensing needles 119. The SNSC 100 of FIG. 6 has three guide tubes with the third tube hidden behind the catheter and not visible in this schematic view. Although the SNSC 100 of FIG. 6 has three guide tubes 115, it is envisioned that other embodiments could have as few as one or as many as eight guide tubes with an optimum number being three or four. A larger diameter target vessel might suggest the use of as many as 4 to 8 guide tubes 115 and sensor tubes 116. The structure of the SNSC 100 is based on the design of the PTAC 100 of FIG. 2 of Fischell et al application Ser. No. 13/752,062, except that the SNSC 100 is used to sense nerve activity instead of deliver ablative fluid into the periadventitial space.

Different shapes are envisioned for the distal openings (or windows) 131 in the outer tube extension 104 where the guide tubes 115 exit. These possible shapes include a racetrack design with curved (e.g., round) proximal and distal ends and straight sides in the axial direction, and oval or round shapes. It is also envisioned that there could be a movable flap covering the opening 131 or a slit that could be opened to make the outer surface of the PTAC smooth for better delivery into the renal artery.

It is a feature of this invention that the guide tubes 115 act as needle guiding elements for the ultra-thin sensing needles 119. Specifically, prior art such as Jacobson that describe curved needles that are advanced outward from a central catheter to penetrate the wall of a target vessel, have needles that are advanced (naked) on their own from the distal end or side of a catheter. Without additional guiding and backup support during advancement, needles that are thin enough to essentially eliminate the risk of bleeding following penetration and withdrawal from the wall of the artery are generally too flimsy to reliably penetrate as desired into the vessel wall. Thus the SNSC 100 of the present application preferably includes needle guiding elements such as the guide tubes 115 that allow the ultra-thin sensor needles 119 to be reliably advanced into the wall of a target vessel to the desired depth.

Figure 7:
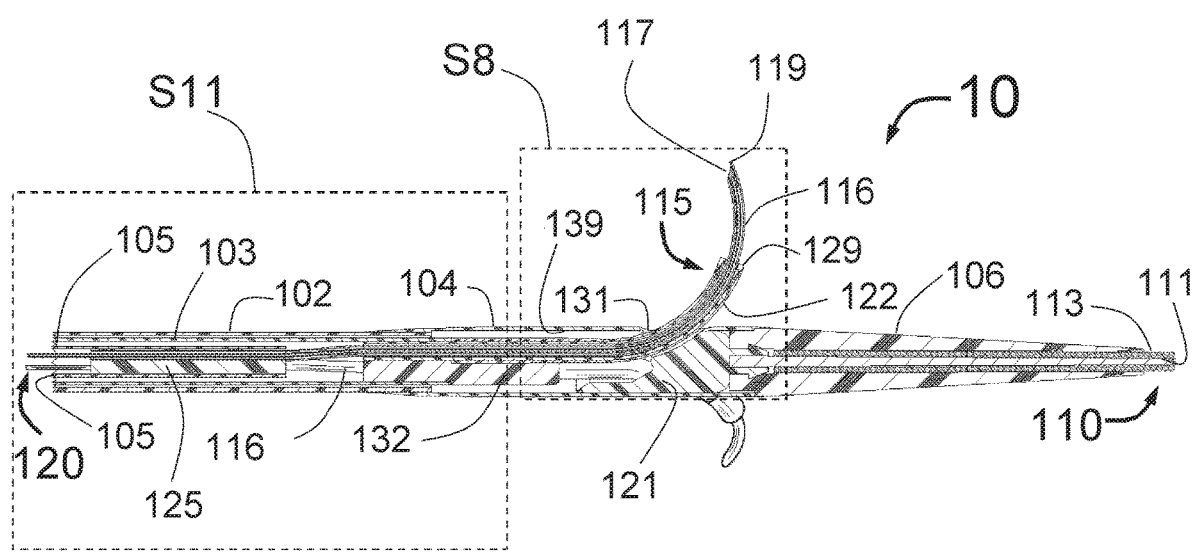
FIG. 7 is a longitudinal cross-section of a distal portion of the SNSC of FIG. 1 in its open position.

FIG. 7 is a longitudinal cross-section of a distal portion of the SNSC 100 as shown in FIG. 6. The proximal end of FIG. 7 shows the three concentric tubes, the outer tube 102, middle tube 103 and inner tube 105 which form the central portion of the SNSC 100. The outer tube 102 is attached to the outer tube extension 104 which is in turn attached to the tapered section 106. The fixed guide wire 110 with core wire 111 and outer layer 113 extends distally from the distal end of the tapered section 106. It should be noted that only part of the length of the guide wire 110 is shown in FIG. 3, its full length is shown in FIG. 6. Enlargements of the sections S4 and S5 of FIG. 3 are shown in FIGS. 4 and 5 respectively.

FIG. 7 shows the guide tube 115 with radiopaque marker 122 in its fully advanced position placed through the opening 131 in the outer tube extension 104. The interior surface of the outer tube extension 104 forms part of the tubular shaft 139 should be made from a stiff material such as a metal or high durometer plastic so that it will be relative rigid as the guide tubes 115 are advanced and retracted.

While it is envisioned that the inner tube 105, middle tube 103 and outer tube 102 could extend proximally to the proximal handle (see FIG. 16) of the SNSC 100 a preferred embodiment of the SNSC 100 of the present application uses four different tubular structures for its outer body instead of just an outer tube 102 and outer tube extension 104. Such was seen in FIG. 5 for the SNSC 10 and is shown in detail in FIG. 15 for the SNSC 100. Just as with the SNSC 10 of FIG. 5 the proximal section would be a metal outer hypotube 82. The outer hypotube would connect at its distal end to a relatively stiff plastic tube 92 about 20 cm long that would in turn connect to a softer more flexible plastic tube about 10 cm long which would is the outer tube 13 for the SNSC 10 of FIGS. 1-5 and is the outer tube 102 of the SNSC 100 of FIGS. 6-8. The plastic tubes 92 and 102 would typically have the same interior and outside diameters. The outer tube extension 104 which is the distal end section of the catheter body typically has a slightly larger inside diameter than the soft outer tube 102. The manifold 125 that connects the inner tube 105 to the sensor tubes 116 is coaxially within the plastic tubes 92 and 102 and at least several centimeters proximal to the outer tube extension 104 which is the distal end section of the catheter body of the SNSC 100.

Figure 15:
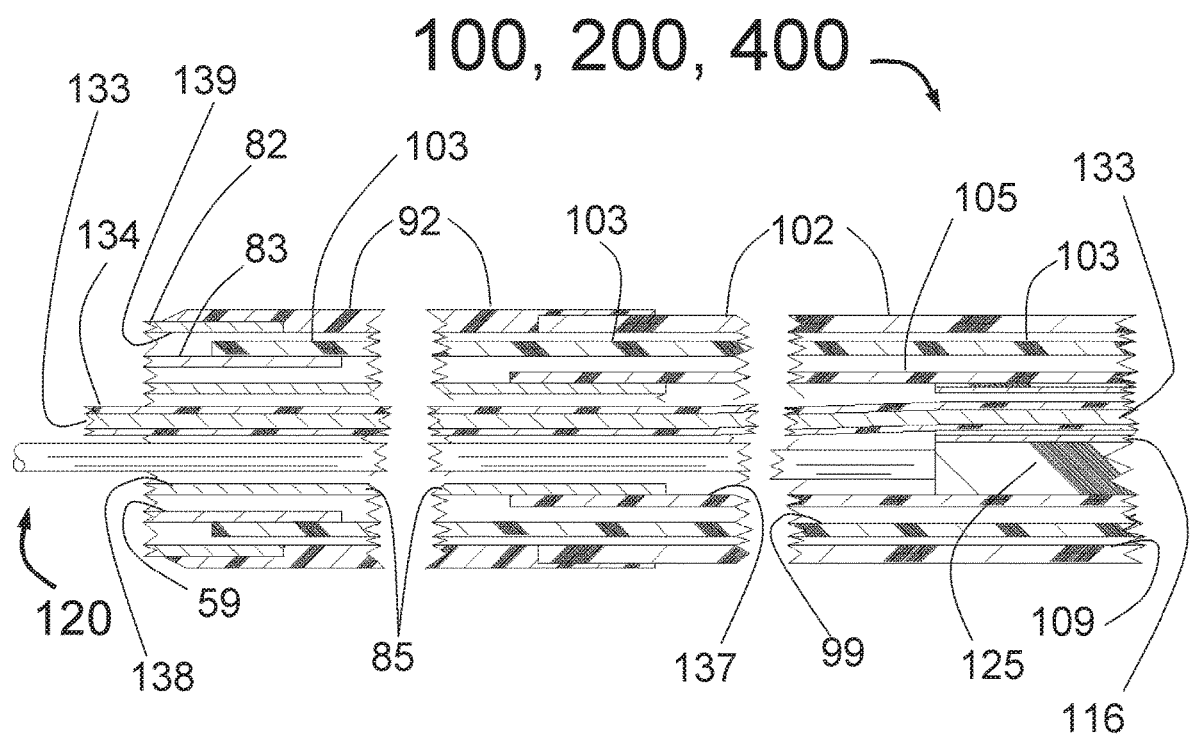
FIG. 15 is a longitudinal cross-section of the central portion of the SNSC/PNASC showing the three proximal hypotubes.

Also in this preferred embodiment, the middle tube 103 attaches to a proximal metal hypotube 83 and the inner tube 105 would also attach to proximal portion formed from a metal inner hypotube 85. The structure of these tubes is shown in FIG. 15.

The central buttress 121 shown in FIG. 7 supports the guide tube 115 both as it is pushed distally, and after it is fully deployed. This central buttress 121 also provides radial support for the advanced guide tubes 115 that prevents the guide tubes 115 from backing away from the interior wall of the target vessel as the sensor tubes 116 are advanced through the guide tubes 115 forward to their desired position 2-6 mm beyond the interior surface of the wall of the target vessel. In exceptional cases, the injection needles 119 at the distal ends of the sensor tubes 116 might be advanced as deep as 10 mm beyond the interior surface of the target vessel. Additional lateral support for the guide tubes 115 is provided by the sides of the openings 131 that in combination with the central buttress 121 provide radial and circumferential/lateral support both during guide tube 115 advancement and outward expansions, and as backup during delivery of the sensor needles 119 through the interior wall of the target vessel. The buttress may comprise a deflection surface such as a curved or linear ramp, which may in a curved embodiment correspond to the radius of curvature of the distal surface of the guide tube 115.

Preferably the radius of curvature of the distal portion of the sensor tubes 116 have a central axis with the same, or nearly the same, radius of curvature as the central axis of the guide tubes 115 and of the central axis of the distal portion of the tubular shaft 139 that is formed within the central buttress 121 when measured in an unconstrained state. In addition, the length of the guide tubes 115 are preferably at least as long as the distal curved portion of the sensor tubes 116 with distal needles 119. This would constrain the curved portion of each injector tube 116 within the lumen of the guide tube 115 so that the injector tube 116 cannot twist or change position.

As seen in FIG. 7 the inner tube 105 connects through the manifold 125 to the three sensor tubes 116, thus the lumens of the sensor tubes 116 are in fluid communication with the lumen of the inner tube. The signal wires 20 exit the proximal end of the sensor tubes 116 and continue in the proximal direction inside of the lumen of the inner tube 105. The inner tube 105 and manifold 125 can slide along the longitudinal axis of the SNSC 100 inside of the middle tube 103 which is shown with uniform diameter over its length including the portion coaxially outside of the manifold 125.

It is clear from the drawing of FIG. 7 that the manifold 125 is located within the lumen of the inner tube 105 in a portion of the tube 105 that is proximal to the distal end of the tube 105. The inner tube 105 and manifold 125 are both located coaxially within the outer tube 102 of the SNSC 100 at a position proximal to the outer tube extension 104 which is the distal end section of the outer body of the SNSC 100. This differs significantly from the embodiment shown in FIG. 3 of the Jacobson U.S. Pat. No. 6,302,870 where the manifold that connects the tube to the needles is attached to the distal end of the tube (instead of being inside it and proximal to the distal end). In addition the Jacobson manifold lies coaxially within the distal end section of the outer body of the catheter (instead of being in the tube that is proximal to the distal end section of the catheter). The distal end section being defined as that distal portion of the catheter from which the needles emerge to curve outward into the wall of a vessel.

Figure 8:
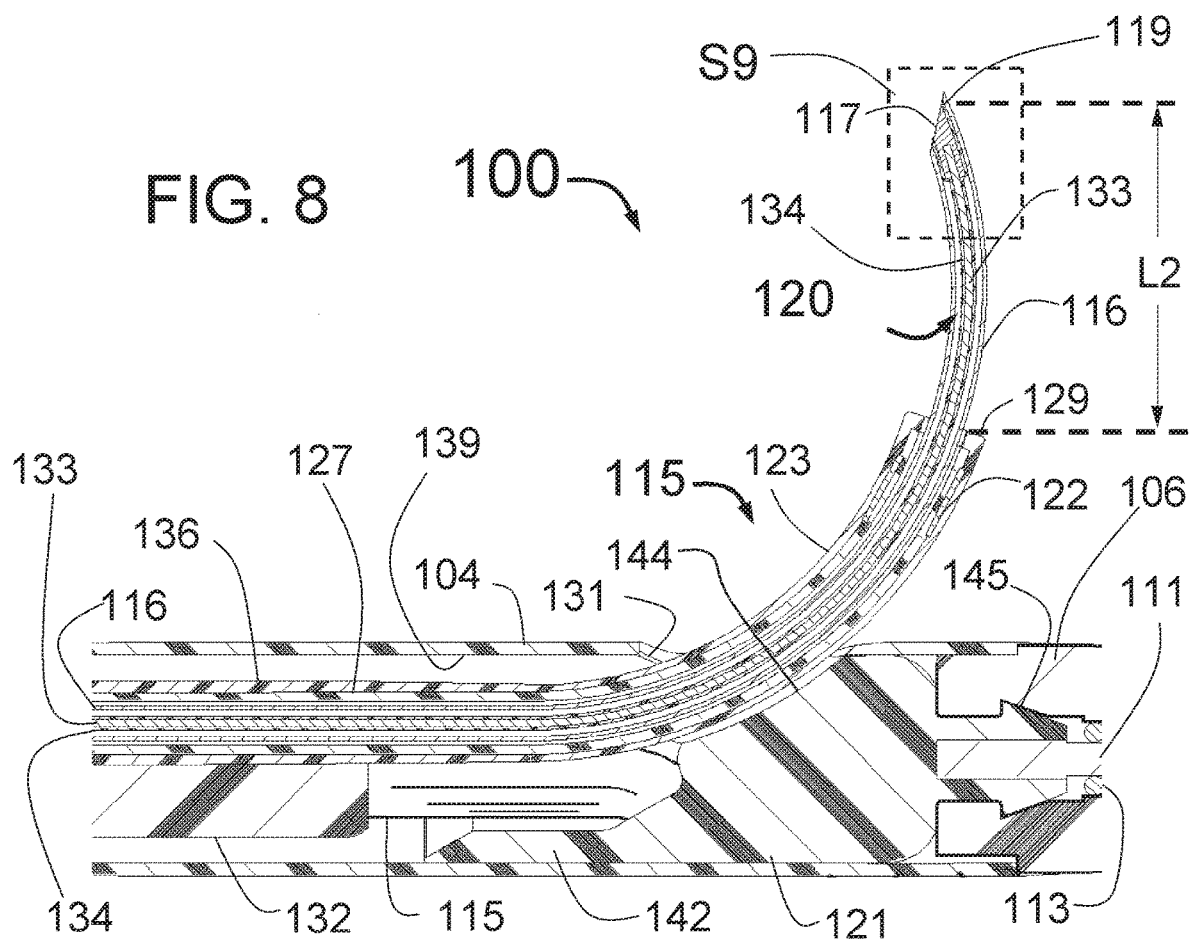
FIG. 8 is an enlargement of region S8 of the SNSC/PNASC of FIG. 2.

The signal wires 120 with core wire 133 and insulation 134 shown in FIG. 8, connect the sensor electrodes 117 to the external equipment outside of the proximal end of the SNSC 100. Detail on the different configurations of the sensor electrodes 117 envisioned for the present invention are shown in FIGS. 9, 10, 12, 13 and 14.

FIG. 8 is the enlargement of section S8 of the longitudinal cross-section of the SNSC 100 as shown in FIG. 7. FIG. 8 shows the details of the guide tubes 115 with interior layer 123, outer layer 127, distal end 129 and radiopaque marker 122. Coaxially within the lumen of the guide tube 115 is the sensor tube 116 with distal sensing needle 119, sensor electrode 117 and sensor wire 120 with core wire 133 and insulation 134. Radiopacity of the distal end of the sensor tubes 116 with distal needles 119 is important so that the operator can confirm under fluoroscopy that the needles 119 have properly deployed into the wall of the target vessel. The present embodiment uses the electrode 117 which would typically be formed from a dense and highly conducting metal such as gold or platinum to provide this radiopacity. It is envisioned however, that other embodiments of the present disclosure may use coatings, plating or markers on the outside and/or inside of the injector tube 116 and needle 119 or the sensor tube 116 with distal needle 119 could be made from a two layer clad material.

The guide tubes 115 are advanced and retracted through the tubular shaft 139 with distal opening 131. The three guide tubes 115 are attached to each other near their proximal ends by the guide tube connector 132. FIG. 8 also clearly shows how the guide tube 115, when advanced against the central buttress 121 is forced outwardly and is supported by the curved ramp 144 of the central buttress 121 as well as the sides of the opening 131 of the tubular shaft 139. The central buttress 121 also has proximal fingers 142 that provide additional lateral support for the guide tubes 115.

The outer tube extension 104 connects at its distal end to the tapered section 106 which in turn lies coaxially around the guide wire 110 (of FIG. 6) with core wire 111 and outer layer 113.

Also shown in FIG. 8 is the penetration depth L2 which is the distance from the distal end 129 of the guide tube 115 to the distal tip of the sensor needle 119. Mechanisms at the proximal end of the SNSC 100 (as shown in FIG. 16) control both the motion of the distal components such as the sensor tubes 116 and guide tubes 115 as well as to limit and/or adjust the penetration depth L2 of the needles 119.

It is envisioned that the central buttress 121 and distal openings 131 can, as shown in FIG. 8, be separate components of the SNSC 100 or they can be formed as a single molded or machined part. The distal tip 145 of the central buttress 121 provides the attachment to secure the buttress 121 to the tapered section 106. Additionally, 121, 131, and 106 could be a single component molded or machined.

While the preferred embodiment of the SNSC 100 has the guide tubes 115 with a pre-formed curved shape, flexible naturally straight guide tubes are also envisioned where the buttress 121 forces the straight guide tubes to curve outward against the interior wall of the target vessel.

The term "central buttress" as used herein includes the, ramp 144 or other deflection surface that provides radial and some lateral support for the deployed guide tubes 115. Specifically, the curved ramp 144 of the buttress 121 supports and guides the outward motion of the guide tubes 115 as they exit though the distal openings 131 and also provide radial support for the guide tubes 115 and injection tubes, as they engage the interior wall of the target vessel. Additional lateral support is provided by the fingers 142 of the central buttress 121 as well as the tubular shaft 139 and the sides of the opening 131. A schematic view of such a central buttress is shown in FIG. 17 of Fischell et al application Ser. No. 13/752,062.

While the central buttress shown in FIG. 8 is a plastic part, a radiopaque metal part, such as stainless steel, or a plastic material that includes radiopaque filler such as tungsten could be advantageously employed for showing the exact location where the guide tubes 115 will exit the SNSC 100. It is also envisioned that a radiopaque marker could be placed or attached to a portion of the openings 131 or buttress 121 or outer tube extension 104 to show the likely spot where the guide tubes 115 and thus the needles 119 would engage the interior wall of the target vessel.

Many of the components of the SNSC 100 are typically made from plastic materials such as polyamide, polyurethane, nylon or tecothane. These include the outer tube 102, middle tube 103 and inner tube 105, the outer tube extension 104, inner layer 127 and outer layer 123 of the guide tubes 115, the tapered section 106, the buttress 121, the guide tube connector 132 and the manifold 125. The manifold 125 can be a molded part or be epoxy or another resin that is injected to glue the sensor tubes together within the lumen of the inner tube 105.

It is also envisioned that any or all of the inner tube 105, middle tube 103 or outer tube 102 could also be a metal hypotube or a metal reinforced plastic tube.

The sensor tubes 116 would typically be made of a springy or shape memory metal such as nitinol. The guide tube radiopaque marker 122 would be made of a radiopaque material such as gold, platinum or tantalum or an alloy of these or similar metals. Any or certain portions of the outside of the SNSC 100 could be lubricity coated to provide improved performance. The sensor tubes 116 and needles 119 should be smaller than 0.5 mm in diameter and preferably less than 0.3 mm in diameter to avoid any blood loss or leakage as the needles penetrate into the wall of the target vessel and are then removed.

Figure 9:
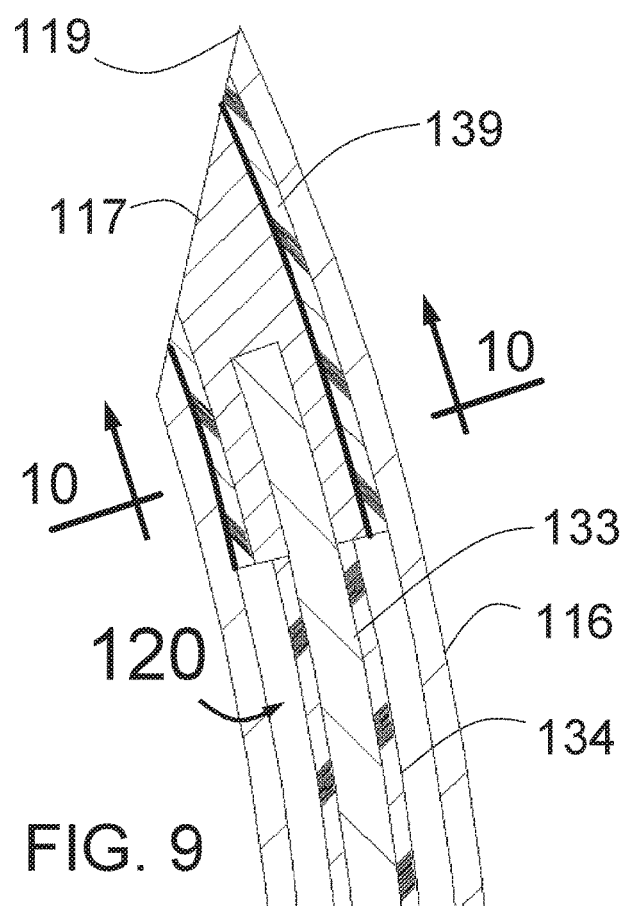
FIG. 9 is an enlargement of region S9 of FIG. 8.

FIG. 9 is a longitudinal cross section showing an enlargement of section S9 of FIG. 8. The sharpened needle 119 at the end of the sensor tube 116 has inserted inside of its end the electrode 117 with insulation 139 that prevents the electrode 117 from coming into electrical contact with the sensor tube 116. The sensor wire 120 with core wire 133 and insulating layer 134 is attached to the electrode 117 as shown with a distal portion of the core wire 133 fixedly attached into a hole in the electrode 117. This can be done using any of a number of mechanical or other techniques including welding, brazing and crimping. Thus voltages sensed by the electrode 117 will be transmitted by the signal wires 120 to the proximal end of the SNSC 100 where external equipment can measure and analyze these signals to provide information relating to sympathetic nerve activity (or the lack thereof) to the user.

One technique for manufacturing the sensing tip configuration of FIG. 9 is to adhesively attach a cylindrical electrode 117 with insulation inside the distal end of a cylindrical sensor tube 116. Allow the adhesive to fix and then cut or grind the sharpened needle until the shape seen in FIG. 9 is produced. Of course one could assemble the parts already sharpened as seen in FIG. 9.

Figure 10:
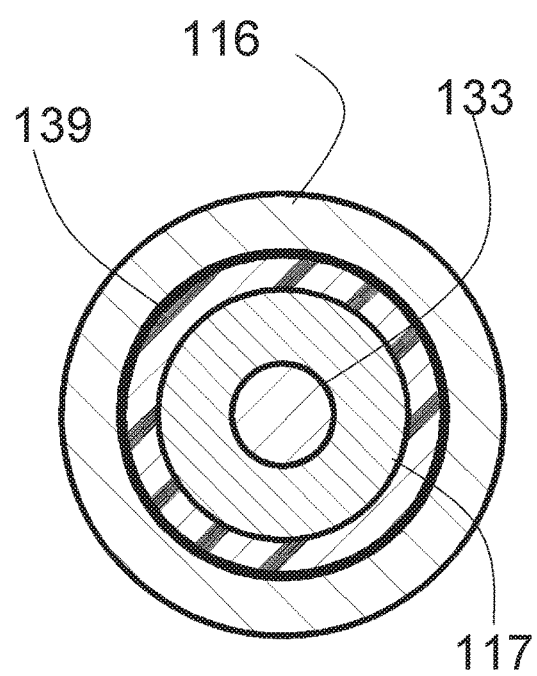
FIG. 10 is a transverse cross section at 10-10 of FIG. 9.

FIG. 10 is a transverse cross section of the distal portion of the sensor tube 116 at 10-10 of FIG. 9. Shown are the sensor tube 116, the insulation 139, electrode 117 and core wire 133.

Figure 11:
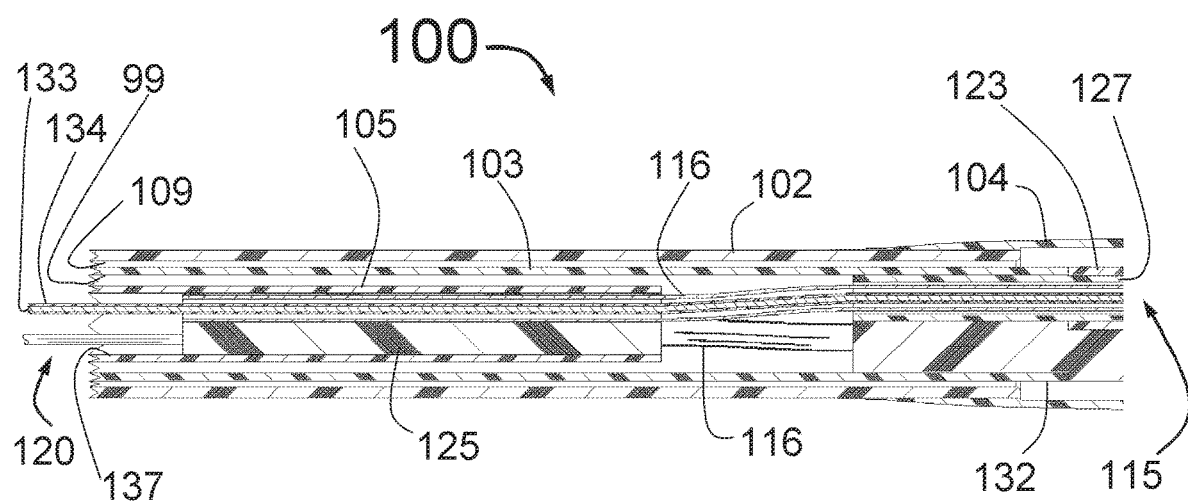
FIG. 11 is an enlargement of region S11 of the SNSC/PNASC of FIG. 2.

FIG. 11 is the enlargement of section S11 of FIG. 7 showing the transition from the central portion to the distal portion of the SNSC 100 including the outer tube 102, middle tube 103 and inner tube 105 with lumen 137. Also shown is the connection between the outer tube 102 and the outer tube extension 104. While the manifold 125 in FIG. 11 shows the proximal end of the sensor tubes 116 at a position distal to the proximal end of the manifold 125, it may be preferable for manufacturing the SNSC 100 with the proximal end of the sensor tubes 116 located at or proximal to the proximal end of the manifold 125.

The guide tube connector 132 connects the three guide tubes 115 to the middle tube 103 that provides the impetus for advancement and retraction of the three guide tubes 115. The motion of the middle tube 103 is produced by the motion of control mechanisms at the proximal end of the SNSC 100. The manifold 125 lies inside of the distal portion of the inner tube 105 and connects together the three sensor tubes 116 so that advancement and retraction of the inner tube 105 provides simultaneous advancement and retraction of the sensor tubes 116. Also shown in FIG. 11 are the flushing spaces between the several tubes. Specifically shown is the outer annular space 109 between the middle tube 103 and the outer tube 102 and the inner annular space 99 between the inner tube 105 and the middle tube 103. Each of these spaces 109 and 99 are to be flushed through with normal saline solution prior to insertion of the SNSC 100 into the patient's body.

It is also visible in FIG. 11 how the proximal end of the injector tube 116 is in fluid communication with the lumen 137 of the inner tube 105.

Also envisioned is a Perivascular Nerve Ablation and Sensing Catheter (PNASC) embodiment of the SNSC 100 of FIGS. 7, 8 and 11 that can both deliver an ablative fluid to the perivascular space as well as sense nerve activity. In this PNASC embodiment the lumen 137 and lumens of the tube 116 outside of the wires 120 can be used for injection of an ablative fluid into the perivascular space through holes in the distal end of the tube 116 shown in the tip configurations 160 of FIG. 13 and 170 of FIG. 14.

The signal wires 120 with core wires 133 and outer insulation 134 that run coaxially within the lumens of the sensor tubes 116 extend proximally from the proximal end of the injector tube 116 to run coaxially within the inner tube 105 all the way to the proximal end of the SNSC 100 where they exit and are enabled to connect to external electronics for measurement of nerve activity.

Longitudinal motion of the inner tube 105 within the uniform diameter middle tube 103 causes the manifold 125 and attached sensor tubes 116 to also move longitudinally. This longitudinal motion caused by control mechanisms near the proximal end of the SNSC 100 will advance and retract the sensor tubes 116 through the lumens of the guide tubes 115 to expand outwardly to penetrate the wall of the target vessel to position the electrodes 117 of FIGS. 6 through 10 at a desirable location to sense sympathetic nerve activity outside of the renal artery.

FIG. 11 also shows how the three sensor tubes 116 extend from the distal end of the inner tube 105 and manifold 125 and then enter the lumen of the inner layer 127 of the guide tube 115 at the proximal end of the guide tube 115. The guide tubes 115 and guide tube connector 132 are attached coaxially within the distal section of the middle tube 103. Thus longitudinal motion of the middle tube 103 will cause longitudinal motion of the guide tube connector 132 and guide tubes 115 thus allowing the mechanism at the proximal section of the SNSC 100 to advance and retract the guide tubes 115 with respect to the outer tube 102 and outer tube extension 104.

It is also envisioned that the penetration depth limitation could be a mechanism that limits the forward motion of the distal end of the inner tube 105 with respect to the guide tube connector 132. A ring or other structure situated between the distal end of the inner tube 105 or manifold 125 and the proximal end of the guide tube connector 132 would limit the forward (distal) motion of the distal end of the inner tube 105 and thus limit penetration of the needles 119 beyond the distal ends 129 of the guide tubes 115. Such a structure could be unattached, or attached to an internal structure of the SNSC 100 shown in FIG. 11 such as the inner tube 105, manifold 125, sensor tubes 116, guide tube connector 132, proximal ends of the guide tubes or the middle tube 103. Such a structure could also have a length adjustment such as screw threads that would allow it to be used to calibrate the penetration depth of the needles 119 beyond the distal ends 129 of the guide tubes 115.

FIG. 12 is a preferred embodiment of the distal tip 150 of the SNSC 100 of FIGS. 6 and 7. In this embodiment the electrode 154 with sharpened needle tip 159 is attached within the distal end of a cylindrical sensor tube 152 with an insulating adhesive 159 to prevent electrical contact between the electrode 154 and the sensor tube 152. The distal end of the electrode 154 can be pre-sharpened or it could be sharpened by cutting or grinding following attachment into the distal end of the sensor tube 152. This configuration has advantage over the tip of FIG. 9 as it provides an electrode with significantly more surface area for picking up nerve activity voltage signals. The same sensor wire 120 with core wire 133 and insulation 134 is attached to the electrode 154.

FIG. 13 is an embodiment of the distal tip 160 of the sensing and fluid injection needle of the PNASC 200 integrated delivery and nerve sensing catheter. Except for the tip 160, the remainder of the PNASC 200 is identical to the SNSC 100 of FIGS. 6, 7, 8 and 11. The tip 160 differs from the tip 150 of FIG. 12 in that side holes 165A and 165B have been placed into the sides of the sensor tube 162 to allow ablative fluid injected at the proximal end of the PNASC 200 to flow through the lumen 137 of the inner tube into the sensor/injection tubes 162 (was 116 in FIG. 11) and then out of one or two or more holes 165A and 165B into the perivascular space. The electrode 164 with needle tip 169 and adhesive attachment layer 159 are identical to that of the electrode 154 and attachment layer 159 of the tip 150 of FIG. 12. The sensor wire 120 is also the same as in FIG. 12 with core wire 133 and insulation 134.

Figure 14:
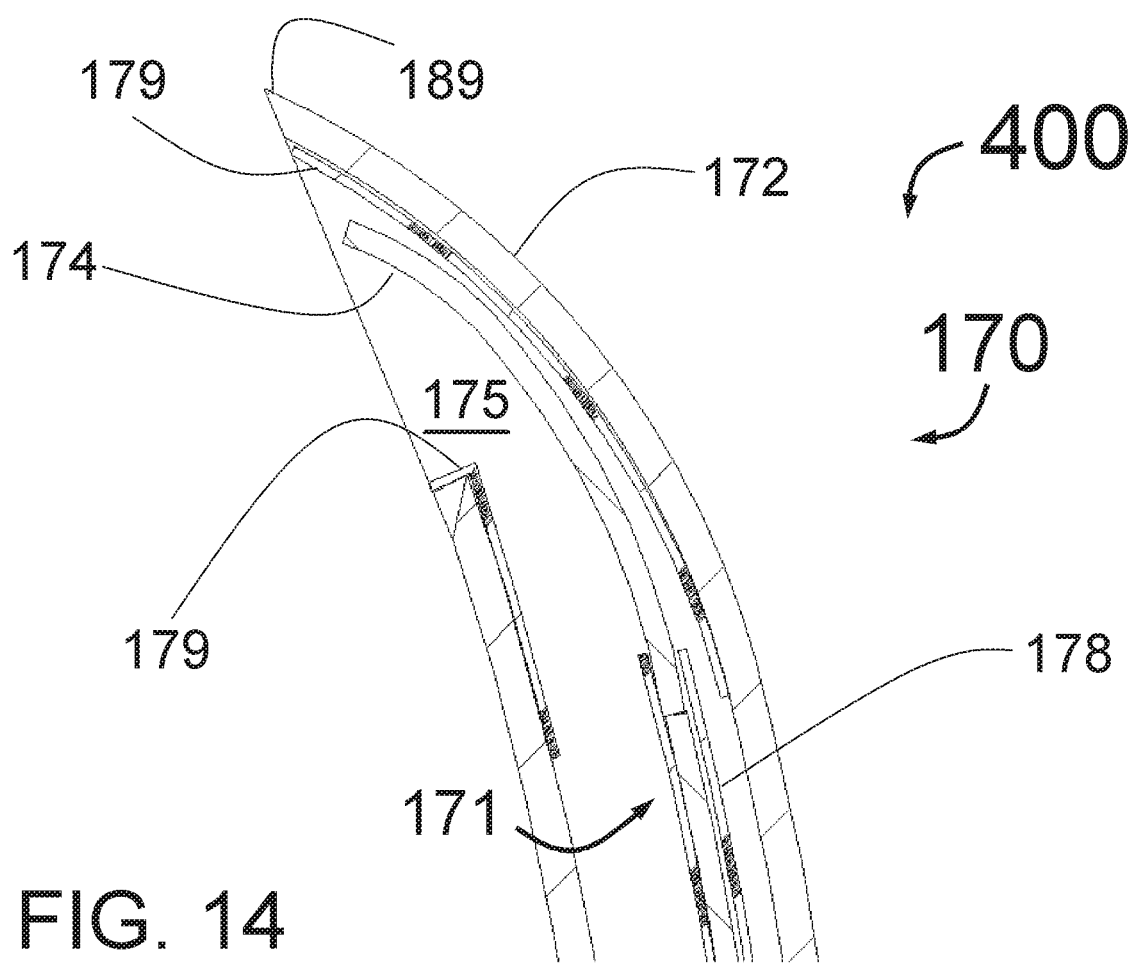
FIG. 14 is a longitudinal cross section of yet another embodiment of the distal portion of the PNASC.

FIG. 14 is another embodiment of the distal tip 170 of the PNASC 400 which can both inject ablative fluid and sense nerve activity. Except for the tip 170, the remainder of the PNASC 400 can be identical to the SNSC 100 of FIGS. 6, 7, 8 and 11. This embodiment uses a non-coring Huber type needle configuration with sharpened needle tip 189 with a turn in the distal end of the sensor/injector tube 172 to prevent coring during penetration. A radiopaque wire 171 with core wire 174 and insulation 178 connects proximally to external equipment. The distal portion of the wire 171 has the insulation removed to allow for the sensing of nerve voltages. To make this work it is necessary to insulate the sensor wire 172 except for the distal portion and where it connects to the external equipment and also insulate the inside of the distal portion 170 of the PNASC 400 to prevent electrical shorting between the sensor/injection tube 172 and the core wire 174. The core wire 174 would typically be made from gold or platinum or an alloy of gold or platinum.

FIG. 15 illustrates longitudinal cross-sections of three central portions of the SNSC 100, PNASC 200 and PNASC 400 of FIGS. 6 through 14. At the proximal end of the central portion of the SNSC/PNASC are three concentric metal hypotubes, an outer hypotube 82, middle hypotube 83 and inner hypotube 85. These are typically made from thin walled metallic tubing such as stainless steel, L605, cobalt chromium or nitinol. The outer hypotube 82 attaches at its distal end to a proximal plastic outer tube 92 typically made from a relatively high durometer plastic, for example polyimide. As seen in the central cross-section of FIG. 15, the proximal plastic tube 92 attaches at its distal end to the proximal end of the outer tube 102 also shown in FIGS. 6 through 8. The outer tube 102 is typically made from a lower durometer/more flexible plastic than the proximal plastic tube 92.

As shown in the proximal section of FIG. 15, the middle hypotube 83 is attached at its distal end to the middle tube 103. As shown in the central section of FIG. 15 the inner hypotube 85 is attached at its distal end to the proximal end of the inner tube 105.

Also shown in distal section of FIG. 15 is the manifold 125 that connects the inner tube 105 to the sensor tube 116 as also shown in FIG. 11. Thus the wires 120 with core wire 133 and insulation 134 exit the proximal end of the sensor tubes 116 and continue in the proximal direction through the inner tube 105 and then proximally to that through the lumen 133 of the inner hypotube 85.

For the PNASC 200 or 400, the inner lumens are used for ablative fluid injection. Specifically, the lumen 138 of the inner hypotube 85 is in fluid communication with the lumen 137 of the inner tube 105 which is in fluid communication with the lumens of the sensor tubes 116 of FIGS. 6-11, or the sensor tubes 152, 162 or 172 of FIGS. 12, 13 and 14 respectively. The 162 and 172 being for the PNASC 200 and 400 where injection of an ablative fluid through the inner hypotube 85 into the inner tube 105 through the tubes 162 or 172 and into the perivascular space through openings in the distal portions of the tubes 162 or 172.

While it is envisioned that the outer tube 102, middle tube 103 and inner tube 105 could run all the way to the proximal end of the SNSC 100 or PNASC 200 or 400, the configuration of FIG. 15 is the preferred embodiment as it provides flexibility where needed near the distal end of the catheter with better control of the motion of the inner and middle tubes 105 and 103 as the metal hypotubes do not compress as they move longitudinally while plastic may.

FIG. 16 is a schematic view of one embodiment of the proximal portion (handle) 300 of the SNSC 10, SNSC 100 or PNASC 200 or PNASC 400. The terms proximal portion 300 and handle 300 will be used interchangeably here. The handle 300 includes the mechanisms for advancing and retracting the needle guiding elements/guide tubes 115 and injector tubes 116 with distal needles 119 during the procedure to position the electrodes 117, 154, 164 and 174 and the needles 119 of the various embodiments of the SNSC 100, PNASC 200 and PNASC 400 within the peri-vascular space. Similarly the handle 300 will do the same to position the distal tips of the sharpened wires 20 of the SNASC 10 of FIGS. 1 though 5 in the perivascular space. Such positioning allows for sensing of sympathetic nerve activity as well as injection of ablative fluid for the PNASC embodiments. The handle 300 also has locking mechanisms activated by first and second control mechanisms such as press-able buttons 332 and 342. Specifically, button 332 when depressed unlocks the motion of the guide tube control cylinder 333 with respect to the outer tube control cylinder 335. The outer tube cylinder 335 is attached to the outer hypotube 82 which is in turn connected to the tube 92 that connects to the outer tube 102 as seen in FIG. 15 or the outer tube 13 of FIG. 5. Thus motion of the handle 300 will move the outer hypotube 82 and thus the outer tube 102 (or 13), transition section 106 (or 16) and guide wire 110 (or 40) of the distal end. The transition section 338 provides strain relief to avoid kinks at the connection between the outer tube control cylinder 335 and the outer hypotube 82.

The guide tube control cylinder 333 is attached to the middle hypotube 83 that in as shown in FIGS. 5 and 15, connects to the middle tube 12 of the SNSC 10 of FIGS. 1-4 or the middle tube 103 of FIGS. 6-8 that in turn is connected to the guide tubes 30 of FIGS. 1-4 or guide tubes 115 of FIGS. 6 through 8. The guide tube control mechanism 330 allows the user of the SNSC/PNASC to control the distal and proximal motion of the guide tubes 30 or 115 and includes the button 332 and the guide tube control cylinder 333. The needle control mechanism 340 allows the user of the SNSC/PNASC to control the distal and proximal motion of the sharpened wires 20 of the SNSC 100 of FIGS. 1-5 or the sensor tubes 116 with distal needles 119 of the SNSC 100 of FIGS. 6-8. The needle control mechanism includes the button 342 and the needle control cylinder 345.

The button 342 when depressed, unlocks the motion of the needle control cylinder 345 with respect to the guide tube control cylinder 333. The needle control cylinder is attached to the inner hypotube 85 of FIG. 15. Moving the needle control cylinder 343 with respect to the guide tube control cylinder 333 will move the inner hypotube 85 which in turn will cause the relative longitudinal motion of the inner tube 105 of FIGS. 6-8 with respect to the middle tube 103 of FIGS. 6 through 8 which causes the advancement and retraction of the sensor tubes 116 with distal needles 119 though the guide tubes 115. This mechanism advances and retracts the electrodes 117 of FIGS. 6-10, as well as the electrodes 154, 164 and 174 of the distal tips shown in FIGS. 12, 13 and 14. Similarly this mechanism would advance and retract the sharpened wires 20 of FIGS. 1-5 by the controlling the relative motion of the inner tube 11 with respect to the middle tube 12.

The handle 300 shown in FIG. 16 has the flushing port 344. Port 344, which would typically have a Luer fitting, is shown with a cap 346. Port 344 is used to flush with saline the annular spaces 139 and 59 as shown in FIG. 15 and in turn will flush the lumens 109 and 99 shown in FIGS. 11 and 15. The injection port 354 which typically has an ablative fluid connector fitting is shown with cap 356. For the PNASC 200 or 400 embodiments, port 354 allows injection of ablative fluid into the lumen 138 of the inner hypotube of FIG. 15 which then will flow into the inner tube 105 and then into the sensor tubes 162 of the PNASC 200 of FIG. 13 and the sensor tube 172 of the PNASC 400 of FIG. 14. The tubes 162 and 172 have openings near or at their distal end to allow flow of the ablative fluid into the perivascular space.

Although FIG. 16 shows one flushing port 344, it envisioned that two or more flushing ports could be used to flush the internal spaces (other than the injection lumen) within the various embodiments of the SNSC and PNASC. It is also envisioned that a single button and cylinder mechanism could replace the two buttons 332 and 342. If this is the case, then a telescoping mechanism, internal to the proximal portion of the handle 300 would, upon advancement of the single button, first advance the guide tubes 115 then advance the sensor tubes 116 with distal needles 119. Retraction of the single button would first retract the needles 119 and then retract the guide tubes 115.

While a standard Luer or Luer lock fitting could be used for the ablative fluid connector fitting for the injection port 354, Fischell et al in U.S. patent application Ser. No. 13/752,062 describes a non-standard fitting that would be advantageous for injection of the ablative fluid. Because of the ablative/toxic nature of the ablative fluid, having a non-standard fitting for the port 354 would reduce the chance of accidentally injecting the ablative fluid into one of the other ports (e.g. 344) or into the standard Luer fitting in the "Y" adapter typically used with a renal guiding catheter. It would also prevent the operator from the potential error of injecting flushing solution or other agents contained in a conventional Luer lock syringe, through the lumen of the injection tubes. It would also be an advantage for the non-standard fitting port 354 to have a smaller lumen than a standard Luer fitting so as to minimize the catheter dead space/internal volume.

The handle 300 also includes a gap adjustment cylinder 348 that when rotated in one direction reduces the penetration depth L1 of FIG. 3 or L2 shown in FIG. 8 which is the distance the wire tip 23 or needles 119 extend beyond the distal ends 34 and 129 of the guide tubes 30 and 115. Rotation in the other direction of the cylinder 348 will increase the penetration depth L1 or L2. It is envisioned that the gap adjustment cylinder 348 could be accessible to the user of the handle 300 with markings on the handle 300 to indicate the distance that will be achieved. This has advantages for use with the SNSC 10 or 100 which is a purely diagnostic catheter so that the depth of electrode placement can be set and then adjusted of more than one depth is desired.

In another embodiment of the handle 300, the gap adjustment cylinder 348 could be accessible only during assembly and testing of the handle 300 at the factory. This fabrication method is designed to ensure a properly calibrated penetration depth L1/L2 that is preset in the factory during manufacturing and testing of each SNSC 10/100 or PNASC 200/400. This ability to calibrate the penetration depth L1/L2 is useful to achieving a good yield during manufacturing. In other words, even with variation of a few millimeters in the relative lengths of the components of the SNSC 10/100 or PNASC 200/400 such as the inner tube 105 and middle tube 103 of the SNSC 100, the distance L1/L2 can be dialed in exactly using the gap adjustment cylinder 348. In this preferred embodiment, the SNSC 10/100 or PNASC 200/400 would be labeled according to the penetration depth L1/L2. For example, the SNSC 100 might be configured to have three different depths L2 of 3 mm, 4 mm and 5 mm. It is also envisioned that a set screw or other mechanism (not shown) could be included to lock the gap adjustment cylinder 348 at the desired penetration depth setting after calibration. While a gap adjustment cylinder 348 is shown here, it is envisioned that other mechanisms such as a sliding cylinder could also be used to adjust the depth L1/L2.

The wires 120 of FIGS. 6 through 13 and the wires 171 of FIG. 14 exit through the side of the most distal portion of the handle 300 as seen in FIG. 16. These three wires (more wires would be used if more electrodes/needles are used) are connected to an electrical connector 220 which in turns connects to the electronics module (not shown) where the voltages between pairs of wires 120 can be measured and displayed. In an alternate embodiment of the SNSC 10 or 100, the wires 120 may exit the proximal section of the handle 300 through the fitting 354 where the cap 356 has been removed.

The function of the handle 300 is to operate the SNSC 10/100 for measurement of the activity of the sympathetic nerves outside of the renal artery before, during and after a renal denervation procedure. With the integrated PNASC 200 or 400, the handle 300 also allows for injection of an ablative fluid to be delivered to the perivascular space.

The procedure using the SNSC 10 or 100 for sympathetic nerve activity measurement would include the following steps although not every step is essential and steps may be simplified or modified as will be appreciated by those of skill in this art:

1. Flush all of the internal volumes of the SNSC 10 or 100 with normal saline through the ports 344 and 354.
2. Insert the distal end of the SNSC 10 or 100 through a previously placed guiding catheter, positioning the distal portion of the SNSC 10 or 100 as at the desired location in the patient's renal artery.
3. Depress the button 332, and while holding the outer tube control cylinder 335 which is locked to the guide tube control cylinder 333, push the guide tube control cylinder 335 in the distal direction advancing the guide tubes 30 or 115 until the distal end of the guide tubes 34 or 129 come into contact with the inside wall of the renal artery limiting the advance of the middle tube 12 of FIG. 3 or 103 of FIG. 8 and deploying the guide tubes 30 or 115 from inside the tubular shafts 21 or 120 and out through the openings 15 or 131. The notch 331 will otherwise stop the distal motion of the guide tube control cylinder 333 when it engages the tube 344 at the maximum allowable diameter for the guide tubes 30 or 115.
4. Release the button 332 which relocks the relative motion of the outer tube control cylinder 335 with respect to the guide tube control cylinder 333.
5. Depress the button 342 that allows relative motion of the needle control cylinder 345 with respect to the guide tube control cylinder 333 and while holding the outer tube control cylinder 335 (which is now locked to the guide tube control cylinder 333) advance the needle control cylinder 345 with distal end 349 until the penetration limiting mechanism stops the motion and the preset depth L1 for the wire tip/needle 23 or L2 for the needles 119 or 159 with respect to the distal ends 34 and 129 respectively of the guide tubes 30 and 115. There are two ways this can be done: 1) The distal end 349 of the needle control cylinder 345 is pushed forward until it engages the guide tube flush port 344 or 2) the internal gap 347 is closed against the proximal end of the gap adjustment cylinder 348 inside the needle control cylinder 345
6. Release the button 342, which relocks the motion of the needle control cylinder 345 to the guide tube control cylinder 333. This places the SNSC 10 or 100 in a configuration where the wire tips 23 or needles 119 or 159 penetrate through the internal elastic lamina (IEL) of the renal artery and penetrate to a preset distance (typically between 2 to 8 mm) beyond the IEL into the perivascular space outside of the media of the renal artery. The depth of 2-6 mm will minimize intimal and medial renal artery injury.

7. Attach the connector 220 to the external nerve activity measurement equipment and measure the amplitude or level of sympathetic nerve activity between at least one pair of electrodes 25 of FIGS. 1-3, or electrodes 117 of FIGS. 6-8, or electrodes 154 of FIG. 12. Alternately if a common ground wire is included in the SNSC 10 or 100 or provided by a skin surface electrode then a measurement between a distal electrode and the common ground can be made. The level of nerve activity should be noted by the user and or might be saved in memory of the external equipment.

8. Depress the button 342 and while holding the outer tube control cylinder 335, pull the needle control cylinder 345 back in the proximal direction until the wire tip/needles 23, 119 or 159 are fully retracted back into the guide tubes 115. It is envisioned that a click or stop would occur when the needle control cylinder 345 reaches the correct position so that the wire tip/needles 23, 119 or 159 are fully retracted.

9. Release the button 342 locking the motion of the injection needle control cylinder 345 to the guide tube control cylinder 333.

10. Depress the button 332 releasing the relative motion of the outer tube control cylinder 335 with respect to the guide tube control cylinder 333 that is now locked to the injection needle control cylinder 345.

11. Retract in the proximal direction the guide tube control cylinder 333 with respect to the outer tube control cylinder 335. This will retract the guide tubes 30 or 115 back inside the openings 131 in the outer body extension 14 or 104 the SNSC 10 or 100.

12. Pull the SNSC 10 or 100 back into the guiding catheter.

13. Move the guiding catheter to the other renal artery.

14. Repeat steps 3 through 12 for the other renal artery.

15. Remove the SNSC 10 or 100 from the body.

16. Perform a renal denervation procedure on both arteries using energy based devices such as the Simplicity™ of Medtronic or the PTAC of Fischell et al Ser. No. 13/752,062 and remove the treatment device from the body.

17. Reinsert the SNSC 10 or 100 through the guiding catheter and repeat steps 3 through 15.

18. Use the difference in nerve activity between before and after the renal denervation procedure to determine the effectiveness of the renal derivation for each artery and repeat steps 16 through 18 as needed until sufficient loss of sympathetic nerve activity is seen.

19. Remove all devices from the body.

Finally, if insufficient drop in blood pressure is seen at follow-up, the SNSC 10 or 100 can be used to assess sympathetic nerve activity as a diagnostic tool.

The procedure using the PNASC 200 or 400 100 for sympathetic nerve activity measurement and renal denervation would include the following steps although not every step is essential and steps may be simplified or modified as will be appreciated by those of skill in this art:

1. Flush the injection lumen with ablative fluid through the port 354 leaving ablative fluid in the dead space within the PNASC 200 or 400. Also flush all of the internal volumes of the PNASC 200 OR 400 with normal saline through the ports 344.

2. Insert the PNASC 200 OR 400 through a previously placed guiding catheter, positioning the distal portion of the PNASC 200 OR 400 at the desired location in one patient's renal artery.

3. Depress the button 332, and while holding the outer tube control cylinder 335 which is locked to the guide tube control cylinder 333, push the guide tube control cylinder 335 in the distal direction advancing the guide tubes 115 until the distal end of the guide tubes 129 come into contact with the inside wall of the renal artery limiting the advance of the middle tube 103 of FIG. 8 and deploying the guide tubes 115 from inside the tubular shafts 120 and out through the openings 131. The notch 331 will otherwise stop the distal motion of the guide tube control cylinder 333 when it engages the tube 344 at the maximum allowable diameter for the guide tubes 115.

4. Release the button 332 which relocks the relative motion of the outer tube control cylinder 335 with respect to the guide tube control cylinder 333.

5. Depress the button 342 that allows relative motion of the injection needle control cylinder 345 with respect to the guide tube control cylinder 333 and while holding the outer tube control cylinder 335 (which is now locked to the guide tube control cylinder 333) advance the needle control cylinder 345 with distal end 349 until the penetration limiting mechanism stops the motion and the preset depth L2 of the needles 169 or 189 with respect to the distal ends 129 of the guide tubes 115. There are two ways this can be done: 1) The distal end 349 of the needle control cylinder 345 is pushed forward until it engages the guide tube flush port 344 or 2) the internal gap 347 is closed against the proximal end of the gap adjustment cylinder 348 inside the needle control cylinder 345

6. Release the button 342, which relocks the motion of the needle control cylinder 345 to the guide tube control cylinder 333. This places the PNASC 200 OR 400 in the configuration where the needles 169 or 189 with electrodes 164 or 174 penetrate through the internal elastic lamina (IEL) and penetrate to a preset distance (typically between 2 to 6 mm) beyond the IEL into the perivascular space outside of the media of the renal artery. The depth of 2-6 mm will minimize intimal and medial renal artery injury.

7. Attach the connector 220 to the external nerve activity measurement equipment and measure the amplitude or level of sympathetic nerve activity between at least one pair of electrodes 164 of FIG. 13, or electrodes 174 of FIG. 14. Alternately if a common ground wire is included in the PNASC 200 or 400 or provided by a skin surface electrode then a measurement between a distal electrode and the common ground can be made. The level of nerve activity should be noted by the user and or might be saved in memory of the external equipment.

8. In this position a syringe or manifold with syringes (not shown) can be attached to the port 354 and the desired volume of ablative fluid is injected. The ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1 to 5 ml. This should produce a multiplicity of ablation zones (one for each injection needle 169 or 189) that will intersect to form an ablative ring around the circumference of the target vessel. The local anesthetic can be at injected at the primary site of injection of ablative fluid, distal or proximal to the primary site. There may be some advantages of injecting an anesthetic proximal to the ablation site. Similarly, the PNASC could be used with an energy delivery renal denervation device to either or both measure nerve activity and inject a local anaesthetic. Use of proximal or distal anesthetic can also apply to prior art devices such as the PTAC of Fischell application Ser. No. 13/752,062. Contrast could be added to the injection either during a test injection before the neuroablative agent or during the therapeutic injection to allow x-ray visualization of the ablation zone. With ethanol, as an ablative agent, a volume of less than 0.6 ml is sufficient for this infusion as it will not only completely fill the needed volume including the sympathetic nerves, but is small enough that if accidentally discharged into the renal artery, would not harm the patient's kidneys. Ideally, a volume of 0.1 ml to 0.3 ml of ethanol should be used. The amount used could be the same for all renal arteries or it could vary depending on the diameter of the renal artery into which the ethanol is to be injected. The agrophobic, hygroscopic and lipophilic nature of ethanol enhances the spread allowing such a small volume to be effective. It is desirable to fluoroscopically verify the deployment of the needles 169 or 189 of FIGS. 13-14 into the vessel wall of the target vessel before injecting the ablative agent or fluid.

9. After waiting up to 30 minutes for the ablative fluid to affect the nerves, re-measure the nerve activity noting the difference in nerve activity between before and after the renal denervation procedure to determine the effectiveness of the renal derivation. Repeat steps 8 and 9 if insufficient loss of nerve activity is seen.

10. Once sufficient nerve damage is determined, depress the button 342 and while holding the outer tube control cylinder 335, pull the needle control cylinder 345 back in the proximal direction until the injection needles 169 or 189 are fully retracted back into the guide tubes 115. It is envisioned that a click or stop would occur when the injection needle control cylinder 345 reaches the correct position so that the injection needles 169 or 189 are fully retracted.

11. Release the button 342 locking the motion of the injection needle control cylinder 345 to the guide tube control cylinder 333.

12. Depress the button 332 releasing the relative motion of the outer tube control cylinder 335 with respect to the guide tube control cylinder 333 that is now locked to the injection needle control cylinder 345.

13. Retract in the proximal direction the guide tube control cylinder 333 with respect to the outer tube control cylinder 335. This will retract the guide tubes 115 of the configuration of FIG. 9 back inside the openings 131 in the outer body extension 104 the PNASC 200 OR 400.

14. Pull the PNASC 200 OR 400 back into the guiding catheter 140.

15. Move the guiding catheter 140 to the other renal artery.

16. Repeat steps 3 through 13 for the other renal artery.

17. Remove the PNASC 200 OR 400 from the body.

Fischell et al U.S. patent application Ser. No. 13/752,062 discloses multiple techniques for use of saline pre and intermediate flushing of the injection lumens of the PTAC 100 which can also be used here.

While the buttons 332 and 342, as described above, release the motion of control cylinders when depressed and lock when released, it is also envisioned that they could also be interlocked as follows:

1. The first interlock allows the injection needle control cylinder 345 to be unlocked only when the guide tube control cylinder 333 is in its most distal position where the outer tube 102 is pulled back and the guide tubes 115 are fully deployed.

2. The second interlock allows the guide tube control cylinder 333 to be unlocked only when the injection needle control cylinder 345 is in its most distal position where the needles 169 or 189 are retracted within the guide tubes 115.

These same interlocks can be applied to the SNSC 10 or 100 of FIGS. 1-12, however the interlocks are more important when associated with the injection of a neurotoxic ablative fluid.

The combination of the buttons 332 and 342 with the control mechanisms described above should make the use of the SNSC 10 or 100 and the PNASC 200 or 400 reasonably simple and straight forward. The operator basically presses button 332 and pushes the guide tube cylinder 333 forward causing the guide tubes 30 or 115 to expand outward, then presses button 342 and advances the needles 23, 119, 169 or 189 forward to penetrate the wall of the renal artery. Nerve activity measurements and/or injections are performed then the reverse procedure is done with button 342 depressed and the needles 23, 119, 169 or 189 retracted, then button 332 is depressed and the guide tube cylinder 333 is retracted in the proximal direction retracting the guide tubes 30 or 115 within the body of the catheter.

While a push-button activated handle where sections are pushed and pulled in the longitudinal direction to cause guide tube and needle deployment is shown in FIG. 16, it is envisioned that other techniques such as rotational mechanisms for locking or longitudinal motion can also be used. The Fischell et al U.S. patent application Ser. No. 13/643,070 filed Oct. 23, 2012, which is hereby incorporated by reference in its entirety, shows such a rotational locking mechanism in FIG. 33.

It should also be noted that in one variation of the procedure having the cap 356 locked onto to the fitting for the injection port 354 prior to placing the PNASC 300 or 400 into the patient's body will certainly prevent any ablative solution from entering the renal artery during insertion of the PNASC 200 or 400 into the renal artery. Additionally, replacing that sealing cap 356 onto the fitting for the injection port 354 as the PNASC 200 or 400 is moved from one renal artery to the opposite renal artery will also prevent any ablative solution from entering the second renal artery. The cap 356 would also be locked onto the fitting for the injection port 354 as the PNASC 200 or 400 is removed from the patient's body. During the renal denervation procedure, the cap 356 would be removed only to inject ablative solution into the peri-vascular space of the treated vessel.

A stopcock attached to the port 354 could also be used such that when closed, it would prevent leakage of ablative fluid out of the needle distal openings of the PNASC 200 or 400. In reality of course, if there were no cap 356 attached as the PNASC 200 or 400 is moved within the arterial system of the body, the blood pressure within the arterial system would if anything force any fluid within the injection lumens of the PNASC 200 or 400 back out of port 354.

The SNSC 10 or 100 and the PNASC 200 or 400 can be packaged with the guide tubes 30 or 115 and the sensor tube 20, 116, 152, 162 or 172 fully extended. The reason for this is that the preferred embodiment of the guide tubes are made from plastic such as polyimide formed into a curve shape. Such a plastic material may lose its shape if it were packaged retracted back into the tubular shaft 21 or 120 which would straighten it. In this case, the device would be shipped in a protective housing to ensure handlers do not receive needle sticks.

It is also possible to ship the device with the needles 23, 119 159, 169 or 189 retracted within the guide tubes 30 or 115 for safety.

Throughout this specification the terms injector tube with distal injection needle is used to specify a tube with a sharpened distal end that penetrates into tissue and is used to inject a fluid into that tissue. Such a structure could also be called a hypodermic needle, an injection needle or simply a needle. In addition, the terms element and structure may be used interchangeably within the scope of this application. The term Luer fitting may be used throughout this application to mean a tapered Luer fitting without a screw cap or a Luer Lock fitting that has a screw cap.

The term needle will be used throughout this disclosure to characterize a small diameter sharpened wire or tube designed to penetrate through the wall of a target vessel, its primary characteristic being a sharpened tip. Thus the distal portion of the sharpened wire as disclosed herein is also a needle.

While this specification has focused on use of the SNSC 10 or 100 and the PNASC 200 or 400 for use in the measurement of nerve activity outside of the renal artery, it is also clearly envisioned that the apparatus and methods of FIGS. 1-16 inclusive can be applied to measure electrical activity outside of any vessel or duct of the human body and in the case of the PNASC 200 or 400, inject any fluid for any purpose including that of local drug delivery into a specified portion of a blood vessel or the volume of tissue just outside of a blood vessel, or into prostatic tissue via the prostatic urethra. For example these devices could be used to assess electrical activity in the wall of the left atrium outside of the Pulmonary vein, and ablate the tissue there to diagnose and treat atrial fibrillation. It could also be used to assess nerve activity around a pulmonary artery, to assist in the treatment of pulmonary hypertension.

While the embodiments shown in FIGS. 1 through 16 show three distal electrodes, the presently disclosed structure can be applied to designs with one needle, two needles or 4 or more needles.

Throughout this specification any of the terms ablative fluid, ablative solution and/or ablative substance will be used interchangeably to include a liquid or a gaseous substance delivered into a volume of tissue in a human body with the intention of damaging, killing or ablating nerves or tissue within that volume of tissue.

Also throughout this specification, the term inside wall or interior surface applied to a blood vessel, vessel wall, artery or arterial wall mean the same thing which is the inside surface of the vessel wall, or the "intimal" surface of the vessel lumen. Also the term injection egress is defined as the distal opening in a needle from which a fluid being injected will emerge. With respect to the injection needle, either injection egress or distal opening may be used here interchangeably.

The terminology "deep to" a structure is defined as beyond or outside of the structure so that "deep to the adventitia" refers to a volume of tissue outside of the adventitia of an artery.

Various other modifications, adaptations, and alternative designs are, of course, possible in light of the above teachings. Therefore, it should be understood at this time that within the scope of the appended claims the invention may be practiced otherwise than as specifically described herein.

What is claimed is:

1. A catheter for placement into a vessel of a human body comprising:
    a catheter body having a central axis extending in a longitudinal direction and also having a central lumen;
    at least two needle guiding elements comprising a preformed curved shape adapted to advance outwardly from the catheter body toward the interior wall of the target vessel;
    at least two needles, at least two electrodes with each of the at least two needles having an electrode, the at least two needles adapted to advance outwardly, guided by the at least two needle guiding elements to penetrate the interior wall of the target vessel, each of the at least two needles comprising a fixed insulation layer, wherein the at least two needle guiding elements are configured to maintain their position against the interior wall of the target vessel as the at least two needles penetrate the interior wall of the target vessel to a target tissue; and
    at least two wires, the at least two wires connecting the at least two electrodes to external equipment outside of the catheter.

2. The catheter of claim 1, where each of the at least two needle guiding elements is a guide tube having a lumen.

3. The catheter of claim 2, where each of the at least two needles is adapted to advance outwardly coaxially through the lumen of the guide tube.

4. The catheter of claim 1, wherein the at least two needle guiding elements comprises at least three needle guiding elements and the at least two needles comprises three needles and the at least two wires comprises three wires.

5. The catheter of claim 1, further including a radiopaque marker attached to or within a portion of a structure selected from the group consisting of: a) a needle of the at least two needles, b) a needle guiding element of the at least two needle guiding elements, and c) the catheter body.

6. A catheter for placement into a target vessel of a human body comprising:
    a catheter body having a lumen;
    at least two needle guiding elements comprising a curved shape adapted to advance outwardly from the catheter body toward the interior wall of the target vessel;
    at least two needles, each of the at least two needles having an electrode, the at least two needles adapted to advance outwardly, guided by the at least two needle guiding elements to penetrate the interior wall of the target vessel, wherein the at least two needle guiding elements are configured to maintain their position against the interior wall of the target vessel as the at least two needles penetrate the interior wall of the target vessel; and
    at least two wires adapted for connecting the at least two electrodes to external equipment outside of the catheter.

7. The catheter of claim 6, where each of the at least two needles guiding element is a guide tube having a lumen.

8. The catheter of claim 7, where each of the at least two needles is adapted to advance outwardly coaxially through the lumen of the guide tube.

9. The catheter of claim 6, wherein the catheter includes the at least two needle guiding elements comprises at least three needle guiding elements and the at least two needles comprises three needles and the at least two wires comprises three wires.

10. The catheter of claim 6, further including a fixed distal guide wire.

11. The catheter of claim 6, further including a radiopaque marker attached to or within a portion of a structure selected from the group consisting of: a) a needle of the at least two needles, b) a needle guiding element of the at least two needle guiding elements, and c) the catheter body.

12. The catheter of claim 6, further including a fluid injection port located near a proximal end of the catheter and at least one opening in a distal portion of at least one needle of the at least two needles, the fluid injection port being in fluid communication with the at least one opening in the at least one needle.

13. The catheter of claim 6, further including a mechanical support structure adapted to support each needle guiding element in a direction selected from the group consisting of: a) radial, in which the mechanical support structure supports the at least two needle guiding elements in a radial direction, and b) lateral, in which the mechanical support structure supports the at least two needle guiding elements in a lateral direction.

14. The catheter of claim 6, where the at least two wires are insulated.

15. A method, comprising:
providing a catheter having a catheter body with a proximal end, a distal end, and a first electrode and a second electrode, the first electrode and the second electrode movable between a retracted position within the catheter body and an extended position for piercing a vessel wall;
providing a first guiding element and a second guiding element, the first electrode coaxial with the first guiding element and the second electrode coaxial with the second guiding element;
positioning the distal end of the catheter at an intravascular site within a patient; advancing the first guiding element and the second guiding element outwardly from the catheter body toward the vessel wall;
advancing the first electrode through the first guiding element and into the vessel wall and advancing the second electrode through the second guiding element and into the vessel wall, wherein the first guiding element and the second guiding element are configured to maintain their position against the vessel wall as the first electrode and the second electrode are advanced into the vessel wall.

16. The method as in claim 15, further including placing the first electrode and the second electrode into electrical communication with an instrument electrically coupled to the proximal end of the catheter.

17. The method as in claim 15, wherein an additional electrode is carried by the catheter.

18. The method as in claim 15, wherein an additional electrode is in contact with the patient's skin.

* * * * *